US007919419B2

(12) United States Patent
Hurley et al.

(10) Patent No.: US 7,919,419 B2
(45) Date of Patent: *Apr. 5, 2011

(54) HIGH STRENGTH AND HIGH ELONGATION WIPE

(75) Inventors: Jeffrey Scott Hurley, Bartlett, TN (US); Brian E. Boehmer, Cordova, TN (US); Alan Jeffrey Campbell, Germantown, TN (US); Jerry Michael Moore, Charlotte, NC (US); Douglas William Vercauteren, Gastonia, NC (US); Barry George Burgess, Huntersville, NC (US); Heather Fielder Horton, Memphis, TN (US)

(73) Assignee: Buckeye Technologies Inc., Memphis, TN (US)

( * ) Notice: Subject to any disclaimer, the term of this patent is extended or adjusted under 35 U.S.C. 154(b) by 21 days.

This patent is subject to a terminal disclaimer.

(21) Appl. No.: 12/265,473

(22) Filed: Nov. 5, 2008

(65) Prior Publication Data

US 2009/0092809 A1 Apr. 9, 2009

Related U.S. Application Data

(63) Continuation of application No. 11/301,636, filed on Dec. 12, 2005, now Pat. No. 7,465,684.

(60) Provisional application No. 60/642,048, filed on Jan. 6, 2005, provisional application No. 60/669,830, filed on Apr. 8, 2005, provisional application No. 60/741,583, filed on Dec. 2, 2005.

(51) Int. Cl.
*D04H 1/00* (2006.01)
*B32B 5/26* (2006.01)

(52) U.S. Cl. ........ 442/361; 442/381; 442/391; 442/392; 442/389

(58) Field of Classification Search .......... 442/361–364, 442/381, 391, 392, 389
See application file for complete search history.

(56) References Cited

U.S. PATENT DOCUMENTS

| | | |
|---|---|---|
| 874,418 A | 12/1907 | McEvoy |
| 2,543,870 A | 3/1951 | Robbins |
| 2,588,533 A | 3/1952 | Johnson |
| 2,861,319 A | 11/1958 | Breen |
| 2,931,091 A | 4/1960 | Breen |
| 2,989,798 A | 6/1961 | Bannerman |
| 3,038,235 A | 6/1962 | Zimmerman |
| 3,081,490 A | 3/1963 | Heynen et al. |
| 3,117,362 A | 1/1964 | Breen |
| 3,121,254 A | 2/1964 | Heynen et al. |

(Continued)

FOREIGN PATENT DOCUMENTS

EP 0480724 3/2003

(Continued)

OTHER PUBLICATIONS

U.S. Appl. No. 09/719,338, filed Jan. 17, 2001, Westphal et al.

(Continued)

*Primary Examiner* — Lynda Salvatore
(74) *Attorney, Agent, or Firm* — Baker Botts L.L.P.

(57) ABSTRACT

The present invention provides high strength nonwoven wipe materials and the process of making the materials. The high strength nonwoven wipe materials contain cellulosic fibers, synthetic fibers, or mixtures thereof, with bicomponent fibers and optionally, a binder. The present invention provides a high strength, high elongation, reduced stiffness nonwoven wipe material with superior tensile strength.

15 Claims, 5 Drawing Sheets

Low bicomponent fiber high pulp layer

High bico fiber layer

Low bicomponent fiber high pulp layers

Commercial Structures 25, 25B, 26, 26B, 29, 32, 35, 38, 41, 42, 44 & 45

U.S. PATENT DOCUMENTS

| Patent Number | | Date | Inventor(s) |
|---|---|---|---|
| 3,163,170 | A | 12/1964 | Gates |
| 3,188,689 | A | 6/1965 | Breen |
| 3,237,245 | A | 3/1966 | Nonami et al. |
| 3,249,669 | A | 5/1966 | Jamieson |
| 3,457,342 | A | 7/1969 | Parr et al. |
| 3,466,703 | A | 9/1969 | Heckrotte |
| 3,469,279 | A | 9/1969 | Hudgell |
| 3,500,498 | A | 3/1970 | Fukuma et al. |
| 3,585,685 | A | 6/1971 | McDermott |
| 3,692,423 | A | 9/1972 | Okamoto et al. |
| 3,716,317 | A | 2/1973 | Williams, Jr. et al. |
| 3,778,208 | A | 12/1973 | Bisset et al. |
| 3,787,162 | A | 1/1974 | Cheetham |
| 3,814,561 | A | 6/1974 | Matsui et al. |
| 3,931,386 | A | 1/1976 | Kimura et al. |
| 3,963,406 | A | 6/1976 | Reker |
| 3,992,499 | A | 11/1976 | Lee |
| 4,021,410 | A | 5/1977 | Koyama et al. |
| 4,052,146 | A | 10/1977 | Sternberg |
| 4,115,989 | A | 9/1978 | Spolnicki |
| 4,217,321 | A | 8/1980 | Campbell |
| 4,237,187 | A | 12/1980 | Raybon, Jr. et al. |
| 4,251,200 | A | 2/1981 | Parkin |
| 4,264,289 | A | 4/1981 | Day |
| 4,296,161 | A | 10/1981 | Kaiser et al. |
| 4,335,066 | A | 6/1982 | Dinius |
| 4,350,006 | A | 9/1982 | Okamoto et al. |
| 4,351,793 | A | 9/1982 | Day |
| 4,366,111 | A | 12/1982 | Dinius et al. |
| 4,370,114 | A | 1/1983 | Okamoto et al. |
| 4,375,447 | A | 3/1983 | Chung |
| 4,375,448 | A | 3/1983 | Appel et al. |
| 4,394,485 | A | 7/1983 | Adur |
| 4,406,850 | A | 9/1983 | Hills |
| 4,434,204 | A | 2/1984 | Hartman et al. |
| 4,445,833 | A | 5/1984 | Moriki et al. |
| 4,529,368 | A | 7/1985 | Makansi |
| 4,582,666 | A | 4/1986 | Kenworthy et al. |
| 4,609,710 | A | 9/1986 | Iohara et al. |
| 4,640,810 | A | 2/1987 | Laursen et al. |
| 4,666,390 | A | 5/1987 | Kenworthy et al. |
| 4,684,576 | A | 8/1987 | Tabor et al. |
| 4,687,610 | A | 8/1987 | Vassilatos |
| 4,717,325 | A | 1/1988 | Fujimura et al. |
| 4,732,552 | A | 3/1988 | Chung |
| 4,743,189 | A | 5/1988 | Samuelson |
| 4,950,541 | A | 8/1990 | Tabor et al. |
| 5,045,401 | A | 9/1991 | Tabor et al. |
| 5,068,079 | A | 11/1991 | Gustafsson |
| 5,076,774 | A | 12/1991 | Farrington et al. |
| 5,082,899 | A | 1/1992 | Sawyer et al. |
| 5,126,199 | A | 6/1992 | Sawyer et al. |
| 5,162,074 | A | 11/1992 | Hills |
| 5,185,199 | A | 2/1993 | Sawyer et al. |
| 5,229,060 | A | 7/1993 | Knox et al. |
| 5,234,550 | A | 8/1993 | Ekholm et al. |
| 5,256,050 | A | 10/1993 | Davies |
| 5,269,049 | A | 12/1993 | Gustafsson et al. |
| 5,336,709 | A | 8/1994 | Antikow et al. |
| 5,372,885 | A | 12/1994 | Tabor et al. |
| 5,456,982 | A | 10/1995 | Hansen et al. |
| 5,486,166 | A * | 1/1996 | Bishop et al. ............ 604/366 |
| 5,505,889 | A | 4/1996 | Davies |
| 5,566,611 | A | 10/1996 | Scheucher et al. |
| 5,582,913 | A | 12/1996 | Simons |
| 5,634,249 | A | 6/1997 | Ballarati |
| 5,660,804 | A | 8/1997 | Ochi et al. |
| 5,693,162 | A | 12/1997 | Gustafsson et al. |
| 5,695,486 | A | 12/1997 | Broughton et al. |
| 5,705,565 | A | 1/1998 | Hughes et al. |
| 5,773,825 | A | 6/1998 | Doyle |
| 5,811,186 | A | 9/1998 | Martin et al. |
| 5,849,232 | A | 12/1998 | Ochi et al. |
| 5,922,163 | A | 7/1999 | Helynranta et al. |
| 5,972,463 | A | 10/1999 | Martin et al. |
| 5,981,410 | A | 11/1999 | Hansen et al. |
| 6,007,653 | A | 12/1999 | Pirinen et al. |
| 6,080,482 | A | 6/2000 | Martin et al. |
| 6,159,335 | A | 12/2000 | Owens et al. |
| 6,171,441 | B1 | 1/2001 | Phillips et al. |
| 6,241,713 | B1 | 6/2001 | Gross et al. |
| 6,284,145 | B1 | 9/2001 | Andersson |
| 6,344,109 | B1 | 2/2002 | Gross |
| 6,353,148 | B1 | 3/2002 | Gross |
| 6,355,079 | B1 | 3/2002 | Sorvari et al. |
| 6,363,580 | B1 | 4/2002 | Srensen et al. |
| 6,403,857 | B1 | 6/2002 | Gross et al. |
| 6,420,626 | B1 | 7/2002 | Erspamer et al. |
| 6,436,231 | B1 | 8/2002 | Graef et al. |
| 6,479,415 | B1 | 11/2002 | Erspamer et al. |
| 6,495,734 | B1 | 12/2002 | Fields et al. |
| 6,559,081 | B1 | 5/2003 | Erspamer et al. |
| 6,562,742 | B2 | 5/2003 | Dutkiewicz et al. |
| 6,562,743 | B1 | 5/2003 | Cook et al. |
| 6,670,035 | B2 | 12/2003 | Pittman et al. |
| 6,726,461 | B2 | 4/2004 | Hyvarinen et al. |
| 6,773,810 | B2 | 8/2004 | Sen et al. |
| 6,783,854 | B2 | 8/2004 | Bond |
| 6,811,716 | B1 | 11/2004 | Stengaard et al. |
| 6,811,871 | B2 | 11/2004 | Sen et al. |
| 6,811,873 | B2 | 11/2004 | Nadkarni |
| 6,838,402 | B2 | 1/2005 | Harris et al. |
| 6,841,245 | B2 | 1/2005 | Chang et al. |
| 6,846,561 | B1 | 1/2005 | Gownder et al. |
| 6,855,422 | B2 | 2/2005 | Magill et al. |
| 7,465,684 | B2 | 12/2008 | Hurley et al. |
| 2002/0013560 | A1 | 1/2002 | Erspamer et al. |
| 2003/0208175 | A1 | 11/2003 | Gross et al. |
| 2004/0121135 | A1 | 6/2004 | Hurley et al. |

FOREIGN PATENT DOCUMENTS

| | | |
|---|---|---|
| EP | 1482081 | 1/2004 |
| WO | WO9612615 | 5/1996 |
| WO | WO0034567 | 6/2000 |

OTHER PUBLICATIONS

U.S. Appl. No. 11/301,636, filed Oct. 9, 2008, Amendment After Final.
U.S. Appl. No. 11/301,636, filed Oct. 9, 2008, Notice of Allowance.
U.S. Appl. No. 11/301,636, filed Sep. 22, 2009, Amendment After Final.
U.S. Appl. No. 11/301,636, filed Jul. 28, 2008, Final Rejection.
U.S. Appl. No. 11/301,636, filed Apr. 9, 2008, Response to Non-Final Rejection.
U.S. Appl. No. 11/301,636, filed Jan. 9, 2008, Non-Final Rejection.

* cited by examiner

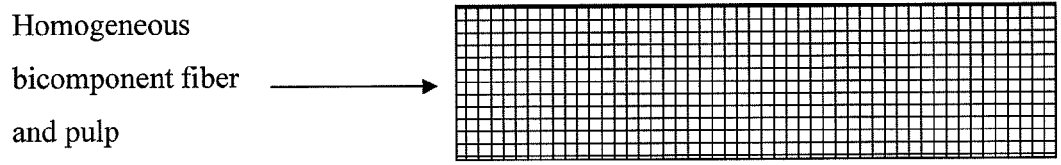
Figure 3. Pilot Homogeneous Structures – Samples 1-10, 21-24, 30, 33, 36, 39 & 52-57
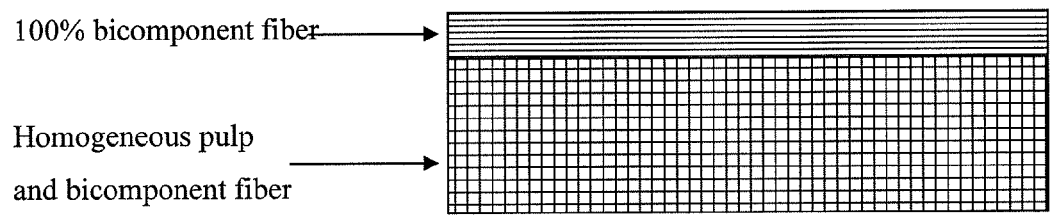
Figure 4. Pilot Layered Structures – Samples 11-20
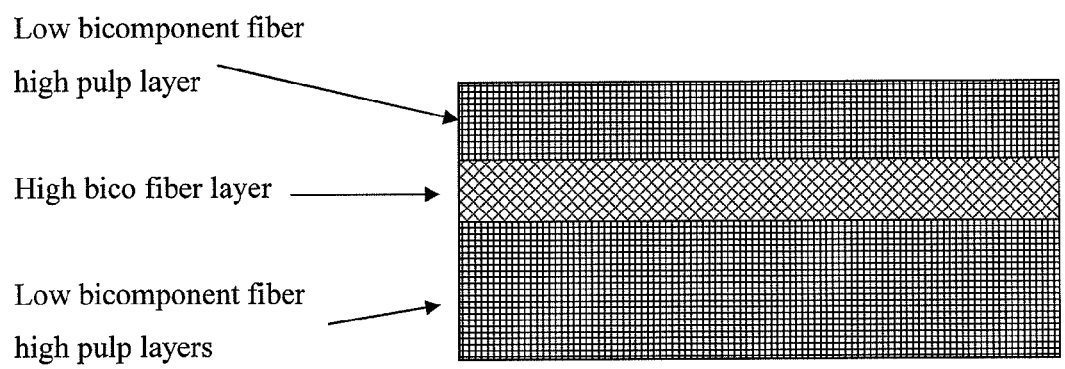
Figure 5. Commercial Structures 25, 25B, 26, 26B, 29, 32, 35, 38, 41, 42, 44 & 45

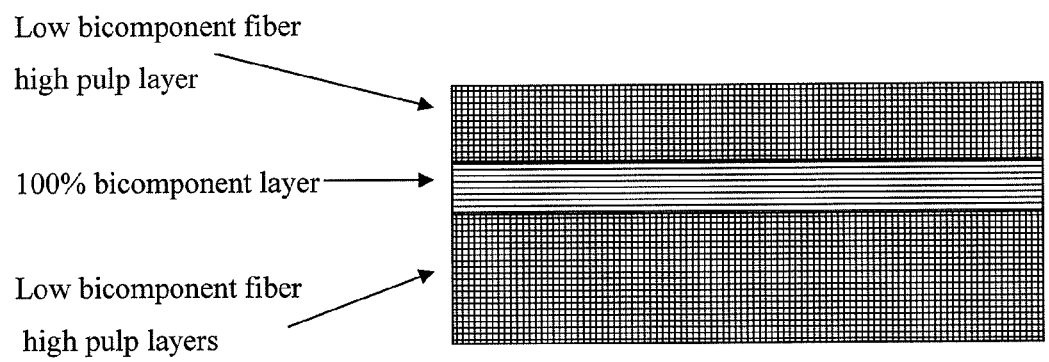
Figure 6. Commercial Structures 27, 27B, 28, 31, 34, 37, 40 & 43
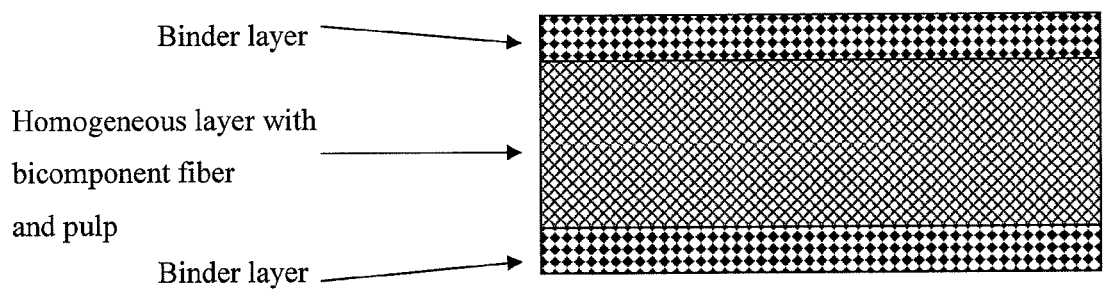
Figure 7. Pilot Homogeneous Structures with Binder– Samples 46 - 51

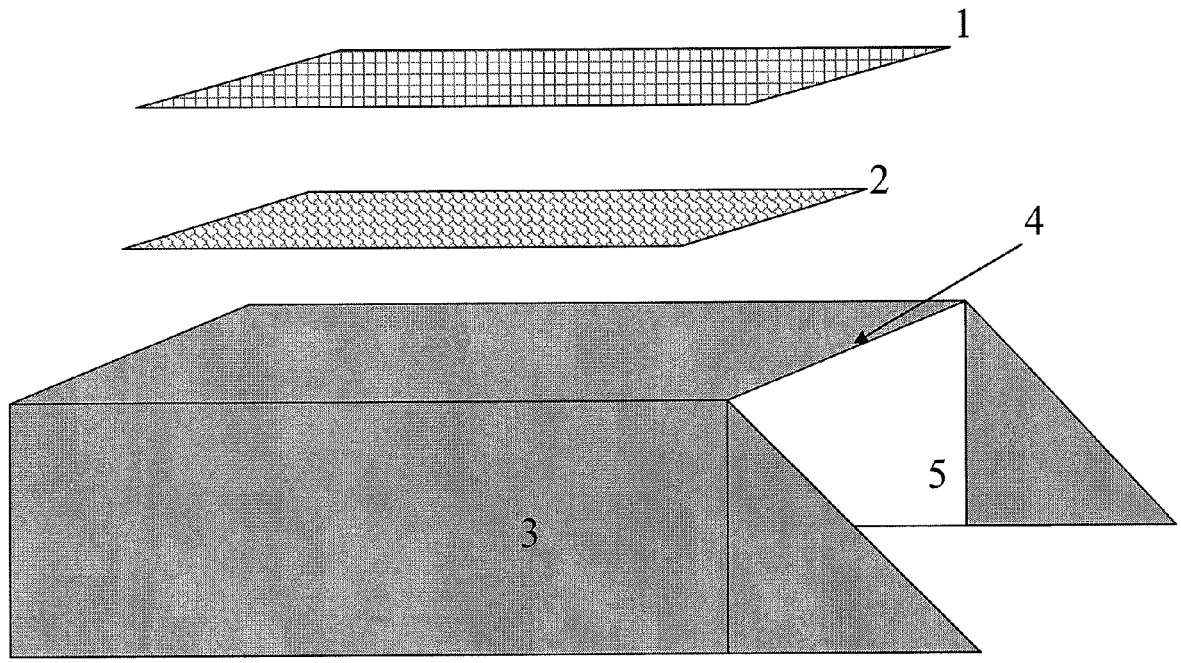
Figure 8. Angular Bend Stiffness Apparatus with Test Sample and Calibrated Slat
100% bicomponent layer →  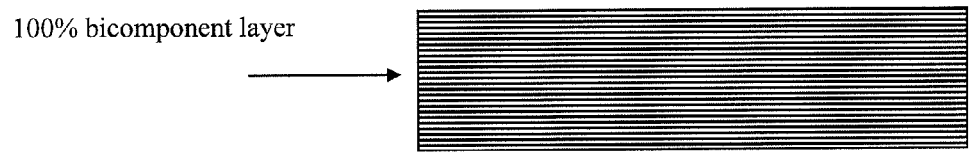
Figure 9. Pilot All Bicomponent Fiber Structure – Sample 52

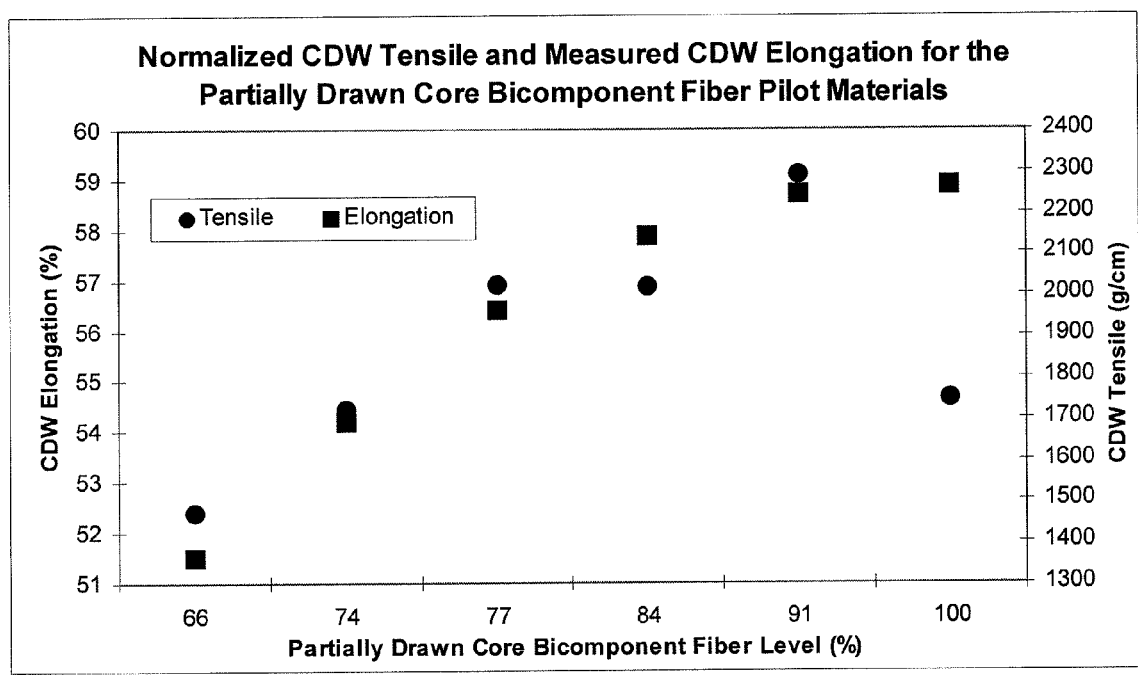
Figure 10. Normalized CDW Tensile and Measured Elongation for the Partially Drawn Core Bicomponent Fiber Pilot Materials

HIGH STRENGTH AND HIGH ELONGATION WIPE

CROSS-REFERENCE TO RELATED APPLICATIONS

This application is a continuation application of U.S. patent application Ser. No. 11/301,636, now U.S. Pat. No. 7,465,684 filed Dec. 12, 2005, which claims priority under 35 U.S.C. §119, based on Application No. 60/642,048, filed Jan. 6, 2005, Application No. 60/669,830, filed Apr. 8, 2005, and Application No. 60/741,583, filed Dec. 2, 2005, all of which are hereby incorporated by reference in their entirety.

FIELD OF THE INVENTION

The present invention relates to high strength nonwoven composite materials and a process for their manufacture.

BACKGROUND OF THE INVENTION

In the manufacture of nonwoven composite materials such as wipes, certain additives have been proposed for specific purposes, such as increasing dry strength, wet strength, dry elongation, wet elongation, improving softness, reducing stiffness or control of wetting properties. In the past, strength agents have been added to paper products in order to increase their strength or otherwise control the properties of the product when contacted with water and/or when used in a wet environment. For example, strength agents are added to paper towels so that the paper towel can be used to wipe and scrub surfaces after being wetted without the towel disintegrating. Wet strength agents are also added to facial tissues to prevent the tissues from tearing when contacting fluids. In some applications, strength agents are also added to bath tissues to provide strength to the tissues during use. When added to bath tissues, however, the wet strength agents should not prevent the bath tissue from disintegrating when dropped in a commode and flushed into a sewer line. Wet strength agents added to bath tissues are sometimes referred to as temporary wet strength agents since they only maintain wet strength in the tissue for a specific length of time.

Although great advancements have been made in providing strength properties to paper products, various needs still exist in the art to increase or to otherwise better control strength and elongation properties and reduce stiffness in certain applications of paper products. For example, a baby wipe that has low strength and/or low elongation can fall apart during use, which can have negative consequences for the user. In addition, current methods of increasing the strength of the wipe typically include the use of more synthetic materials that are higher in cost, usually resulting in a stiffer product, are less environmentally friendly, and have less absorbent capacity for holding liquid or semi-liquid materials.

A need exists for a cost-effective nonwoven composition that provides high strength, high elongation and reduced stiffness properties to a fibrous material, such as a wipe, while simultaneously retaining high performance and absorbency.

SUMMARY OF THE INVENTION

The present invention provides for a high strength, high elongation, reduced stiffness nonwoven wipe material with superior tensile strength, thus providing more protection for the user during use while also reducing cost and reducing the consumption of synthetic materials.

Current commercial baby wipes of this type typically have Cross Direction Wet (CDW) tensile strengths of approximately 177 g/cm (450 g/in) while the present invention is capable of delivering tensile strengths of up to and over 256 g/cm (650 g/in), and even up to and over 455 g/cm at equivalent synthetic content. Current commercial baby wipes of this type typically have a CDW elongation of about 25% while this present invention is capable of delivering a CDW elongation of up to and over 50% at equivalent or lower synthetic content. Additionally, current wipe materials of this type typically have a high angular bend stiffness of over 135 mm while the present invention is capable of delivering an angular bend stiffness of about 100 mm or lower at an equivalent synthetic content.

In one embodiment, the invention is a high strength nonwoven wipe material having
  (A) from about 45 to about 95 weight percent matrix fibers selected from the group consisting of cellulosic fibers, synthetic fibers, and a mixture of cellulosic fibers and synthetic fibers;
  (B) from about 5 to about 55 weight percent bicomponent fiber, wherein the bicomponent fiber has a length of from about 3 mm to about 36 mm; and
  (C) optionally, from about 0 to about 15 weight percent binder,
wherein the weight percentages are based on the total weight of the material, and wherein the material has
  (D) a basis weight of from about 40 gsm to about 100 gsm;
  (E) a density of from about 0.03 to about 0.15 g/cc; and
  (F) a CDW tensile strength of about 147 g/cm or greater.

In other embodiments of the invention, the material has a CDW tensile strength of about 194 g/cm or greater, preferably about 208 g/cm or greater, more preferably about 239 g/cm or greater, more preferably about 252 g/cm or greater, and even more preferably about 681 g/cm or greater. In alternative embodiments, the material has a CDW tensile strength of about 394 g/cm or greater, preferably about 591 g/cm or greater, and more preferably about 787 g/cm or greater.

In certain embodiments, the bicomponent fibers have a partially drawn core.

In a different embodiment of the invention, the high strength multistrata nonwoven wipe material has:
  (A) from about 45 to about 95 weight percent matrix fibers selected from the group consisting of cellulosic fibers, synthetic fibers, and a mixture of cellulosic fibers and synthetic fibers;
  (B) from about 5 to about 55 weight percent bicomponent fiber, wherein the bicomponent fiber has a length of from about 3 mm to about 36 mm; and
  (C) optionally, from 0 to about 15 weight percent binder,
wherein weight percentages are based on the total weight of the material, and wherein the material has
  (D) a basis weight of from about 40 gsm to about 100 gsm,
  (E) a density of from about 0.03 to about 0.15 g/cc, and
  (F) a CDW tensile strength of about 252 g/cm or greater, and
wherein the material has at least one stratum comprising from about 60 weight percent to about 100 weight percent bicomponent fibers.

In certain embodiments, the material further has two or more distinct strata where the composition of any one stratum is different from at least one adjacent stratum. In another embodiment, the material has two outer strata and one or more inner strata, and the matrix fiber of the inner strata comprises bicomponent fibers. In other embodiments, the material has two outer strata and one or more inner strata and the weight percent bicomponent fiber of the inner stratum or strata is greater than the weight percent bicomponent fiber in the outer strata.

In particular embodiments, wherein the material has two outer strata and one or more inner strata, the weight percent bicomponent fiber of one inner stratum is from about 70 weight percent to about 100 weight percent bicomponent fiber based on the total weight of the one inner stratum, preferably from about 70 weight percent to about 95 weight percent bicomponent fiber, more preferably from about 75 weight percent to about 95 weight percent bicomponent fiber, more preferably from about 80 weight percent to about 90 weight percent bicomponent fiber. In other embodiments, wherein the material has two outer strata and one or more inner strata, the weight percent bicomponent fiber of one inner stratum is from about 90 weight percent to about 100 weight percent bicomponent fiber based on the total weight of the one inner stratum.

In another embodiment of the invention, the high strength nonwoven wipe material includes:
(A) from about 0 to about 10 weight percent matrix fibers selected from the group consisting of cellulosic fibers, synthetic fibers, and a mixture of cellulosic fibers and synthetic fibers;
(B) from about 90 to about 100 weight percent bicomponent fiber, wherein the bicomponent fiber has a partially drawn core; and
(C) optionally, from 0 to about 15 weight percent binder, wherein weight percentages are based on the total weight of the material, and wherein the material has
(D) a basis weight of from about 40 gsm to about 100 gsm,
(E) a density of from about 0.03 to about 0.15 g/cc,
(F) a CDW tensile strength of from about 1,200 g/cm or higher, and
(G) a CDW elongation of from about 50% to about 60%.

In yet another embodiment, the high strength nonwoven material including
(A) from about 0 to about 40 weight percent of a matrix fiber,
(B) from about 60 to about 100 weight percent bicomponent fiber, wherein the bicomponent fibers range in length from about 3 mm to about 36 mm and
(C) optionally, up to about 8 weight percent of an emulsion polymer binder,
wherein the nonwoven material has
(D) a basis weight from about 40 gsm to about 100 gsm and
(E) a density from about 0.03 g/cc to about 0.15 g/cc
(F) and a CDW tensile strength of from about 1,200 g/cm to about 2,000 g/cm or greater, and
(G) the CDW elongation of the material ranges from about 50% to about 60%.

The bicomponent materials in the present invention have a length from about 6 mm or greater, about 8 mm or greater, preferably 10 mm or greater, and preferably about 12 mm or greater.

The invention is also directed to a process for the production of a wipe material of one of the previous claims includes airlaying from about 45 to about 90 weight percent of a matrix fiber which includes cellulosic fibers, synthetic fibers or a mixture of cellulosic fibers and synthetic fibers; and from about 5 to about 55 weight percent bicomponent fiber to form material with one or more strata, wherein the material has at least one internal stratum comprising from about 60 weight percent to about 100 weight percent bicomponent fibers, wherein the bicomponent fibers range in length from about 3 mm to about 36 mm, and wherein the CDW tensile strength of the nonwoven material is from about 90 g/cm to about 2,600 g/cm.

In another embodiment, the process for the production of a wipe material of one of the previous claims includes airlaying from about 45 to about 95 weight percent matrix fibers which includes cellulosic fibers, synthetic fibers or a mixture of cellulosic fibers and synthetic fibers, from about 5 to about 55 weight percent bicomponent fiber having a length of from about 3 mm to about 36 mm, and optionally, from 0 to about 15 weight percent binder, wherein weight percentages are based on the total weight of the material, and where the material has a basis weight of from about 40 gsm to about 100 gsm, a density of from about 0.03 to about 0.15 g/cc, and a CDW tensile strength of about 147 g/cm or greater.

In an alternative embodiment, the process for the production of a wipe material of one of the previous claims includes airlaying from about 45 to about 95 weight percent matrix fibers which includes cellulosic fibers, synthetic fibers or a mixture of cellulosic fibers and synthetic fibers, from about 5 to about 55 weight percent bicomponent fiber having a length of from about 3 mm to about 36 mm, and optionally, from 0 to about 15 weight percent binder, wherein weight percentages are based on the total weight of the material, and wherein the material has a basis weight of from about 40 gsm to about 100 gsm, a density of from about 0.03 to about 0.15 g/cc, and a CDW tensile strength of about 252 g/cm or greater, and where the material has a stratum comprising from about 60 weight percent to about 100 weight percent bicomponent fibers.

In another embodiment, the process for the production of a wipe material of one of the previous claims including airlaying: from about 0 weight percent to about 40 weight percent of a matrix fiber, and from about 60 weight percent to about 100 weight percent bicomponent fiber to form material with one or more strata, and optionally, up to about 8 weight percent binder, wherein weight percentages are based on the total weight of the material, and wherein the material has a basis weight of from about 40 gsm to about 100 gsm, a density of from about 0.03 to about 0.15 g/cc, and wherein the bicomponent fibers range in length from about 3 mm to about 36 mm, and wherein the CDW tensile strength of the material of about 1,200 g/cm or greater, and wherein the CDW elongation ranges from about 50% to about 60%.

Preferably, the nonwoven material of the invention has been produced by an airlaid process. In certain embodiments, the bicomponent fibers is deposited by one forming head.

Preferably, the nonwoven material of the invention may be used as a component of a wide variety of absorbent structures, including but not limited to diapers, feminine hygiene materials, incontinent devices, surgical drapes and associated materials, as well as wipes and mops.

These and other aspects of the invention are discussed more in the detailed description and examples.

BRIEF DESCRIPTION OF THE DRAWINGS

FIG. 3 depicts the cross section of a wipe material which is a homogenous structure containing a mixture of bicomponent fibers and pulp. This cross section is representative of Samples 1-10, 21-24, 30, 33, 36, 39, 52 and 53-57 presented in the Examples.

FIG. 4 depicts the cross section of a wipe material which is a layered structure, where one layer is 100% bicomponent fibers and a second layer is made of a mixture of bicomponent fibers and pulp. This cross section is representative of Samples 11-20 presented in the Examples.

FIG. 5 depicts the cross section of a wipe material which is a layered commercial structure having a first layer of a mixture of low bicomponent fiber content and high pulp content, a second layer of high bicomponent fiber content, and a third layer of a mixture of low bicomponent fiber content and high pulp content. This cross section is representative of Samples 25, 25B, 26, 26B, 29, 32, 35, 38, 41, 42, 44 and 45 presented in the Examples.

FIG. 6 depicts the cross section of a wipe material which is a layered commercial structure having a first layer of a mixture of low bicomponent fiber content and high pulp content, a second layer of 100% bicomponent fiber content, and a third layer having a mixture of low bicomponent fiber content and high pulp content. This cross section is representative of Samples 27, 27B, 28, 31, 34, 37, 40 and 43 presented in the Examples.

FIG. 7 depicts the cross section of a wipe material which is a layered pilot structure having a first layer of binder, a second homogenous layer of a mixture of bicomponent fiber and pulp, and a third layer of binder. This cross section is representative of Samples 46-51 in the Examples.

FIG. 8 depicts the angular bend stiffness apparatus as used to determine the stiffness of samples. The top piece labeled "1" is the slat that is calibrated in millimeters. The test sample is labeled "2" and is below the slat. The angular bend stiffness apparatus is labeled "3" and is below the sample. The leading edge of the angular bend stiffness apparatus closest to the 45 degree slope labeled "4". The plane of the 45 degree sloped side of the angular bend stiffness apparatus is labeled "5".

FIG. 9 depicts the cross section of a wipe material which is 100% bicomponent fiber. This cross section is representative of Sample 52 presented in the Examples.

FIG. 10 depicts the normalized CDW tensile strength and elongation of a structure containing partially drawn core bicomponent fibers. The percentage of partially drawn core bicomponent fibers is represented on the x-axis (%); the percentage of CDW elongation (%) is represented on the first y-axis as square data plots; and the CDW tensile strength (g/cm) is represented on the second y-axis as circle data plots.

DETAILED DESCRIPTION OF THE INVENTION

Figure 1:
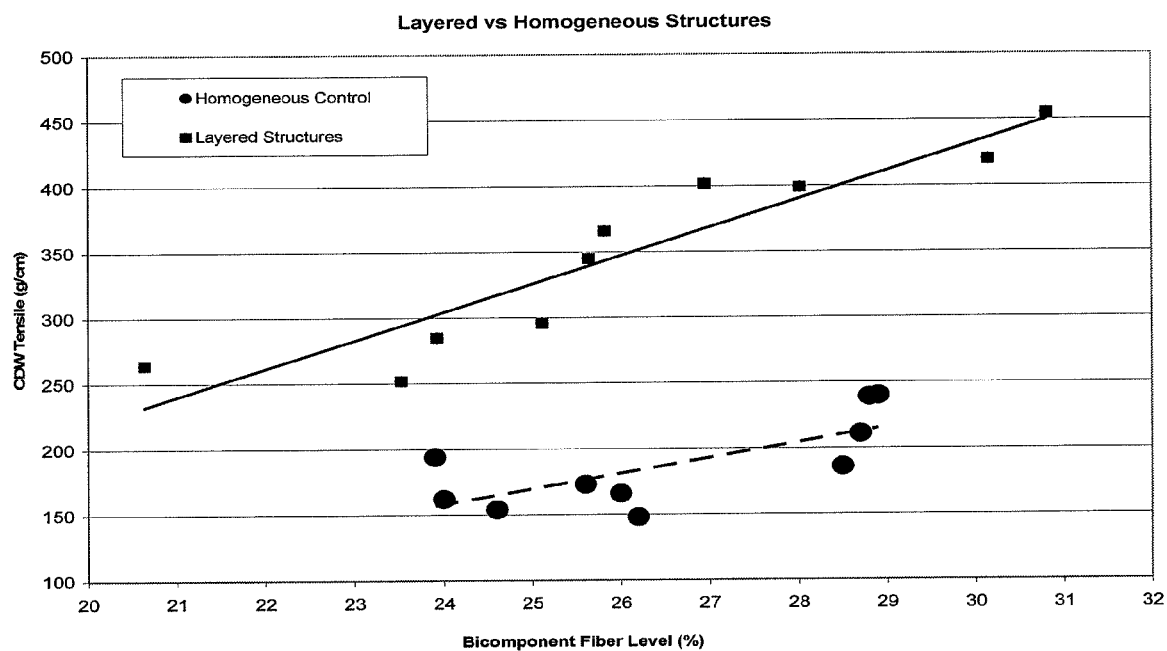
FIG. 1 depicts enhanced tensile strength as the level of bicomponent fibers increase. The figure shows Cross Direction Wet (CDW) (g/cm) over percent bicomponent fibers between control and layered structures.

The present invention provides for a high strength nonwoven wipe material which includes bicomponent fibers, a binder, and commercially available fluff pulp.

Definitions

As used herein, "nonwovens" refer to a class of material, including but not limited to textiles or plastics. "Wipes" are therefore a sub-class of the nonwovens.

The term "weight percent" is meant to refer to the quantity by weight of a compound in the material as a percentage of the weight of the material or to the quantity by weight of a constituent in the material as a percentage of the weight of the final nonwoven product.

The term "basis weight" as used herein refers to the quantity by weight of a compound over a given area. Examples of the units of measure include grams per square meter as identified by the acronym (gsm). In the present invention, the basis weight of the nonwoven material ranges from about 25 gsm to about 250 gsm, preferably from about 40 gsm to about 100 gsm. More preferably, the basis weight of the nonwoven material ranges from about 50 gsm to about 75 gsm.

As used herein, the terms "high strength" or "high tensile strength" refer to the strength of the material. At a minimum, the present material has a 20% increase in Cross Direction Wet (CDW) strength. The CDW tensile strength of the nonwoven material ranges from about 90 g/cm to about 2,600 g/cm. In certain embodiments, the CDW tensile strength ranges from about 98 g/cm to about 984 g/cm. Preferably, the tensile strength is over about 100 g/cm, more preferably over about 147 g/cm.

In particular embodiments, depending on the amount of the bicomponent makeup of the nonmaterial woven, the CDW tensile strength is about 100 g/cm or greater, preferably about 147 g/cm or greater, preferably about 194 g/cm or greater, preferably about 208 g/cm or greater. In other embodiments, the CDW tensile strength is about 239 g/cm or greater, preferably about 252 g/cm or greater, preferably about 326 g/cm or greater, or up to about 394 g/cm or greater, or up to about 591 g/cm or greater, up to about 681 g/cm or greater, or up to about 787 g/cm or greater. In particular embodiments where the bicomponent fiber content is about 60 weight percent or higher, the tensile strength may be about 1,200 g/cm or higher, preferably about 1,700 g/cm or higher, more preferably from about 2,000 g/cm or higher.

The density of the nonwoven material refers to the density of the entire nonwoven material. The density of the nonwoven material ranges from about 0.03 to about 0.15 g/cc.

The integrity of the material can be evaluated by a CDW tensile strength test described for example as follows. A sample is cut perpendicular to the direction in which the airlaid nonwoven is being produced on the machine. The sample should be four inches long and one inch wide. The sample is folded in half and submerged in water to the midpoint for a period of 5 seconds. The sample is then placed in the grips of a tensile tester. A typical tensile tester is an EJA Vantage 5 produced by Thwing-Albert Instrument Company (Philadelphia, Pa.). The grips of the instrument are pulled apart by an applied force from a load cell until the sample breaks. The tensile tester records the force required to break the sample. This number is reported as the cross direction wet tensile. Cross directional wet tensile is reported as the acronym CDW and the typical units are grams per centimeter derived from the amount of force (in grams) over the width of the sample (in centimeters).

As used herein, the term "high elongation" refers to the elongation of the material. At a minimum, the present material has a 15% increase in CDW Elongation percentage. Preferably, the CDW elongation percentage of the material ranges from about 15% to about 100%, preferably from about 15% to about 50%, preferably over 25%. In another embodiment, the CDW elongation percentage of the material ranges from about 50% to about 60%. The CDW elongation percentage is calculated by the same method as the CDW tensile strength. CDW elongation is given as a percentage of the total distance the sample is displaced relative to the starting length.

As used herein, the term "low stiffness" refers to the stiffness of the material as tested by the angular bend stiffness method. At a minimum, the present material has a 25% decrease in angular bend stiffness. Preferably, the angular bend stiffness of the material ranges from about 50 mm to 120 mm, preferably less than 110 mm. The stiffness of the material can be evaluated by a Cross Direction (CD) angular bend stiffness test described for example as follows. The angular bend stiffness device is shown in FIG. 8. A sample is cut perpendicular to the direction in which the airlaid nonwoven is being produced on the machine, also known as the cross direction (CD). The sample should be 300 mm long and 50.8 mm wide. The sample is then placed on the top of the angular bend stiffness device such that the leading edge of the narrow portion of the sample strip is aligned evenly with the edge of the Angular Bend Stiffness device on the 45 degree sloped side of the device. A 300 mm long by 60 mm wide flat strip with calibrations in millimeters along the length of the 300 mm edge is then placed on top of the sample, also known as the slat. The slat is aligned such that the 50.8 mm wide side is the leading edge and is aligned evenly with the edge of the sample and the Angular Bend Stiffness device as shown in FIG. 8. The sample and the calibrated slat are then slowly moved horizontally across the surface, maintaining contact with the surface of the angular bend stiffness device at all times. The sample is extended out across the edge until it is suspended in air above the 45 degree sloped side of the angular bend stiffness device. The sample and the slat are continually moved in this manner until the sample starts to bend downwards. When the sample has been moved a sufficient distance over the leading edge such that the sample has bent enough for its leading edge to break the plane of the 45 degree slope then the distance it has been moved is recorded in millimeters as given on the slat. A stiffer product will give a higher angular bend stiffness in millimeters and a more drapeable product will give a lower angular bend stiffness in millimeters.

As used herein, the term "filament" means a continuous structure such as the form that a fiber initially has during the spinning, drawing, crimping and other steps of the manufacturing process prior to the cutting step.

As used herein, the term "fiber" means a filament that has been cut into smaller segments such as what occurs to a filament or a number of filaments, also known as a tow, when the filament is cut during the manufacturing process. A fiber may also be formed by other methods.

As used herein, the term "partially drawn core" or "partially drawn fiber" means all or part of a fiber, such as with a bicomponent fiber, has not been drawn or stretched to achieve the highest possible tenacity or strength in its fiber form, but that some degree of drawing or stretching has been done to induce some degree of orientation or crystallinity and strength into the fiber. Thus, a partially drawn core bicomponent fiber or a partially drawn homopolymer is still capable of being stretched or drawn further once incorporated into an article. This allows the partially drawn core bicomponent fiber or partially drawn homopolymer to provide additional strength and elongation to the article as it is further drawn while incorporated within the article, such as a wet wipe. A homopolymer or bicomponent fiber is typically stretched close to the point of failure as this induces a high level of crystallinity and strength into the fiber form. The drawing or stretching of the filament, before it is cut into fibers, can occur in both the spinning and drawing steps. Drawing during the spinning step, also known as the draw-down, occurs when the molten fiber is pulled from the face of the spinneret resulting in drawing of the spun filament. For example, a commercially available 2.0 dpf bicomponent fiber, such as Trevira 1661, would have an elongation of or about 40% while a partially drawn core bicomponent fiber such as Trevira T255 with a 2.0 dpf would have an elongation of or about 100% or greater. Some degree of drawing is required in order to prevent the as-spun filament from becoming embrittled due to aging, which can cause a catastrophic failure, such as breaking, during the drawing step. Numerous examples of spinning and drawing homopolymer and bicomponent fibers are disclosed in U.S. Pat. Nos. 4,115,989, 4,217,321, 4,529,368, 4,687,610, 5,185,199, 5,372,885 and 6,841,245. Numerous examples of producing fibers, yarns and other melt spun or extruded materials that are referred to as undrawn, but that have some drawing during the melt spinning phase where the polymer is pulled away from the face of the spinneret and numerous examples of producing fibers, yarns and other melt spun or extruded materials where little or no tension is applied to the filaments as they leave the face of the spinneret, for example adhesive polymers, are formed and are referred to as undrawn are disclosed in U.S. Pat. Nos. 3,931,386, 4,021,410, 4,237,187, 4,434,204, 4,609,710, 5,229,060, 5,336,709, 5,634,249, 5,660,804, 5,773,825, 5,811,186, 5,849,232, 5,972,463 and 6,080,482.

As used herein, the term "about" or "approximately" mean within an acceptable error range for the particular value as determined by one of ordinary skill in the art, which will depend in part on how the value is measured or determined, for example, the limitations of the measurement system. For example, about or approximately can mean within 1 or more than 1 standard deviations, per the practice in the art. Alternatively, about or approximately can mean a range of up to 20%, preferably up to 10%, more preferably up to 5%, and more preferably still up to 1% of a given value. Alternatively, the term can mean within an order of magnitude, preferably within 5-fold, and more preferably within 2-fold, of a value.

As used herein, the term "melt spinning" means a process where molten polymer is extruded through a spinneret or die into a filament that may subsequently be converted into individual fibers via cutting. Melt spinning can utilize polymers that originate via a continuously fed process or via chip form where the chip is heated to a molten state. In both cases, the molten polymer or polymers are pumped at a specified flow rate through a spinneret. A spinneret is plate with holes, usually made of metal or ceramics, with the number of holes and hole sizes varying depending on the type of fiber desired. The spinneret may also contain a filtration media that can act as both a filter and a static mixer to give a more uniform product. After the molten polymer or polymers are pumped through the spinneret it forms a filament that is quenched or cooled almost immediately with a medium that will efficiently remove the heat from the molten polymer or polymers. This will allow the filaments to maintain there shape as a filament for future steps in the fiber forming process. The continuous filaments that are pulled from the face of the spinneret and are brought together to form a tow, which is essentially a bundle of filaments. The process by which the filaments are taken away from the face of the spinneret, which is essentially pulling, results in a slight orientation within the polymer as this pulling results in some drawing of the fiber. The tow, now also referred to as a spun yarn, is then ready for subsequent steps in the fiber forming process, including, but not limited to drawing.

As used herein, the term "drawing" means a process where the filament or filaments from the melt spinning step, which now may be referred to as a tow or spun yarn, are mechanically pulled, stretched or drawn. This results in a decreased diameter for the individual filaments in the tow while also increasing molecular orientation and increasing tensile strength. Heat is generally applied to assist in the drawing of the tow. Drawing may be accomplished by passing the tow over rolls of increasing speeds that will pull the individual filaments of the tow and cause their diameter to decrease, helping to align individual polymer chains within the filament, also stated as giving the molecular orientation that results in enhanced tensile strength. Subsequent steps may also include heat setting, crimping, cutting and baling.

The prior definitions do not limit the scope of this invention as spinning and drawing may also occur in a consecutive process and or the spinning process may be optimized such that it provides the majority of the drawing of the filament and or the drawing step may provide the majority of the drawing of the filament. Any of these various methods for drawing the filament could be applied to produce the partially drawn core bicomponent and homopolymer fibers referenced here within. In addition there are other methods for producing partially drawn fibers that are known in the art.

Nonwoven Materials

The matrix fibers of the present invention may be natural, synthetic, or a mixture thereof. In one embodiment, the fibers may be cellulose-based fibers, one or more synthetic fibers, or a mixture thereof. Any cellulose fibers known in the art, including cellulose fibers of any natural origin, such as those derived from wood pulp, may be used in a cellulosic layer. Preferred cellulose fibers include, but are not limited to, digested fibers, such as kraft, prehydrolyzed kraft, soda, sulfite, chemi-thermal mechanical, and thermo-mechanical treated fibers, derived from softwood, hardwood or cotton linters. More preferred cellulose fibers include, but are not limited to, kraft digested fibers, including prehydrolyzed kraft digested fibers. Suitable for use in this invention are the cellulose fibers derived from softwoods, such as pines, firs, and spruces. Other suitable cellulose fibers include those derived from Esparto grass, bagasse, kemp, flax, hemp, kenaf, and other lignaceous and cellulosic fiber sources. Suitable cellulose fibers include, but are not limited to, bleached Kraft southern pine fibers sold under the trademark FOLEY FLUFFS® (Buckeye Technologies Inc., Memphis, Tenn.).

The nonwoven materials of the invention may also include a commercially available bright fluff pulp including, but not limited to, southern softwood fluff pulp (such as Treated FOLEY FLUFFS®) northern softwood sulfite pulp (such as T 730 from Weyerheuser), or hardwood pulp (such as eucalyptus). The preferred pulp is Treated FOLEY FLUFFS® from Buckeye Technologies Inc. (Memphis, Tenn.), however any absorbent fluff pulp or mixtures thereof may be used.

In one embodiment of this invention, matrix fibers suitable for use in the structures of the invention may include cellulosic or synthetic fibers or blends thereof. Most preferred is wood cellulose. Also preferred is cotton linter pulp, chemically modified cellulose such as crosslinked cellulose fibers and highly purified cellulose fibers, such as Buckeye HPF (each available from Buckeye Technologies Inc., Memphis, Tenn.). The fluff fibers may be blended with synthetic fibers, for example polyester such as PET, nylon, polyethylene or polypropylene.

Bicomponent fibers having a core and sheath are known in the art. Many varieties are used in the manufacture of nonwoven materials, particularly those produced by airlaid techniques. Various bicomponent fibers suitable for use in the present invention are disclosed in U.S. Pat. Nos. 5,372,885 and 5,456,982, both of which are hereby incorporated by reference in their entirety. Examples of bicomponent fiber manufacturers include Invista (Salisbury, N.C.), Trevira (Bobingen, Germany) and ES Fiber Visions (Athens, Ga.).

Bicomponent fibers may incorporate a variety of polymers as their core and sheath components. Bicomponent fibers that have a PE (polyethylene) or modified PE sheath typically have a PET (polyethyleneterephthalate) or PP (polypropylene) core. In one embodiment, the bicomponent fiber has a core made of polyester and sheath made of polyethylene. The denier of the bicomponent fiber preferably ranges from about 1.0 dpf to about 4.0 dpf, and more preferably from about 1.5 dpf to about 2.5 dpf.

The length of the bicomponent fiber is from about 3 mm to about 36 mm, preferably from about 4 mm to about 24 mm, more preferably from about 5 mm to about 18 mm, and even more preferably from about 6 mm to about 12 mm. In preferred embodiments, the bicomponent fibers are about 6 mm or greater, preferably about 8 mm or greater, more preferably about 10 mm or greater, and more preferably about 12 mm or greater.

Various geometries can be used for the bicomponent fiber of this invention, including concentric, eccentric, islands-in-the-sea, and side-by-side. The relative weight percentages of the core and sheath components of the total fiber may be varied.

Various degrees of stretching, drawing or draw ratios can be used for the bicomponent fiber in this invention, including partially drawn and highly drawn bicomponent fibers and homopolymers. These fibers can include a variety of polymers and may have a partially drawn core, a partially drawn sheath or a partially drawn core and sheath or they may be a homopolymer that is partially drawn.

Bicomponent fibers are typically fabricated commercially by melt spinning. In this procedure, each molten polymer is extruded through a die, e.g., a spinneret, with subsequent pulling of the molten polymer to move it away from the face of the spinneret, solidification of the polymer by heat transfer to a surrounding fluid medium, for example chilled air, and taking up of the now solid filament. Additional steps after melt spinning may also include hot or cold drawing, heat treating, crimping and cutting. This overall manufacturing process is generally carried out as a discontinuous two step process that first involves spinning of the filaments and their collection into a tow that comprises numerous filaments. During the spinning step, when molten polymer is pulled away from the face of the spinneret, some drawing of the filament does occur which may also be called the draw-down. This is followed by a second step where the spun fibers are drawn or stretched to increase molecular alignment and crystallinity and to give enhanced strength and other physical properties to the individual filaments. Subsequent steps may include heat setting, crimping and cutting of the filament into fibers. The drawing or stretching step may involve drawing the core of the bicomponent fiber, the sheath of the bicomponent fiber or both the core and the sheath of the bicomponent fiber depending on the materials from which the core and sheath are comprised as well as the conditions employed during the drawing or stretching process. Bicomponent fibers may also be formed in a continuous process where the spinning and drawing are done in a continuous process. In accordance with standard terminology of the fiber and filament industry, the following definitions apply to the terms used herein:

Convenient references relating to fibers and filaments, including those of man made thermoplastics, and incorporated herein by reference, are, for example: (a) Encyclopedia of Polymer Science and Technology, Interscience, New York, vol. 6 (1967), pp. 505-555 and vol. 9 (1968), pp. 403-440; (b) Kirk-Othmer Encyclopedia of Chemical Technology, vol. 16 for "Olefin Fibers", John Wiley and Sons, New York, 1981, 3rd edition; (c) Man Made and Fiber and Textile Dictionary, Celanese Corporation; (d) Fundamentals of Fibre Formation—The Science of Fibre Spinning and Drawing, Adrezij Ziabicki, John Wiley and Sons, London/New York, 1976; and (e) Man Made Fibres, by R. W. Moncrieff, John Wiley and Sons, London/New York, 1975.

Numerous other processes are involved before, during and after the spinning and drawing steps and are disclosed in U.S. Pat. Nos. 4,950,541, 5,082,899, 5,126,199, 5,372,885, 5,456,982, 5,705,565, 2,861,319, 2,931,091, 2,989,798, 3,038,235, 3,081,490, 3,117,362, 3,121,254, 3,188,689, 3,237,245, 3,249,669, 3,457,342, 3,466,703, 3,469,279, 3,500,498, 3,585,685, 3,163,170, 3,692,423, 3,716,317, 3,778,208, 3,787,162, 3,814,561, 3,963,406, 3,992,499, 4,052,146, 4,251,200, 4,350,006, 4,370,114, 4,406,850, 4,445,833, 4,717,325, 4,743,189, 5,162,074, 5,256,050, 5,505,889, 5,582,913, and 6,670,035, all of which are hereby incorporated by reference in their entirety. Fully drawn bicomponent fibers are currently produced on the commercial scale by companies such as, but not limited to Invista (Salisbury, N.C.), Wellman (Fort Mill, S.C.), Trevira (Bobingen, Germany) and FiberVisions (Varde, Denmark). Fully drawn is defined as being drawn or stretched close to the maximum level of drawing or stretching such that it will induce a high degree of molecular orientation in the fiber, and with it enhanced strength in the fiber form, without overdrawing or over-stretching such that the fiber has a catastrophic failure and potentially breaks. The present invention has shown that fibers that are not fully drawn or stretched, such as what is currently practiced on the commercial scale by the aforementioned companies and others practicing this art, can enhance the tensile and elongation properties of the final article relative to the same article that uses the current commercially produced bicomponent fibers that have been fully drawn. The present invention includes articles that contain bicomponent fibers that are partially drawn with varying degrees of draw or stretch, highly drawn bicomponent fibers and mixtures thereof. These may include a highly drawn polyester core bicomponent fiber with a variety of sheath materials, specifically including a polyethylene sheath such as Invista T255 (Salisbury, N.C.) and Trevira T255 (Bobingen, Germany) or a highly drawn polypropylene core bicomponent fiber with a variety of sheath materials, specifically including a polyethylene sheath such as ES FiberVisions AL-Adhesion-C (Varde, Denmark). Additionally, Trevira T265 bicomponent fiber (Bobingen, Germany), having a partially drawn core with a core made of polybutylene terephthalate (PBT) and a sheath made of polyethylene may be used.

The bicomponent fibers of the present invention may also include fibers that utilize a partially drawn polyester core with a variety of sheath materials, specifically including a polyethylene sheath. The use of both partially drawn and highly drawn bicomponent fibers in the same structure can be leveraged to meet specific physical and performance properties based on how they are incorporated into the structure. The bicomponent fibers of the present invention are not limited in scope to any specific polymers for either the core or the sheath as any partially drawn core bico fiber could provide enhanced performance regarding elongation and strength. The degree to which the partially drawn bicomponent fibers are drawn is not limited in scope as different degrees of drawing will yield different enhancements in performance. The scope of the partially drawn bicomponent fibers encompasses fibers with various core sheath configurations including, but not limited to concentric, eccentric, side by side, islands in a sea, pie segments and other variations. In addition, the scope of this invention covers the use of partially drawn homopolymers such as polyester, polypropylene, nylon, and other melt spinnable polymers. The scope of this invention also covers multicomponent fibers that may have more than two polymers as part of the fibers structure.

Other synthetic fibers suitable for use in various embodiments as matrix fibers or as bicomponent binder fibers include fibers made from various polymers including, by way of example and not by limitation, acrylic, polyamides (such as, for example, Nylon 6, Nylon 6/6, Nylon 12, polyaspartic acid, polyglutamic acid, and so forth), polyamines, polyimides, polyacrylics (such as, for example, polyacrylamide, polyacrylonitrile, esters of methacrylic acid and acrylic acid, and so forth), polycarbonates (such as, for example, polybisphenol A carbonate, polypropylene carbonate, and so forth), polydienes (such as, for example, polybutadiene, polyisoprene, polynorbornene, and so forth), polyepoxides, polyesters (such as, for example, polyethylene terephthalate, polybutylene terephthalate, polytrimethylene terephthalate, polycaprolactone, polyglycolide, polylactide, polyhydroxybutyrate, polyhydroxyvalerate, polyethylene adipate, polybutylene adipate, polypropylene succinate, and so forth), polyethers (such as, for example, polyethylene glycol (polyethylene oxide), polybutylene glycol, polypropylene oxide, polyoxymethylene (paraformaldehyde), polytetramethylene ether (polytetrahydrofuran), polyepichlorohydrin, and so forth), polyfluorocarbons, formaldehyde polymers (such as, for example, urea-formaldehyde, melamine-formaldehyde, phenol formaldehyde, and so forth), natural polymers (such as, for example, cellulosics, chitosans, lignins, waxes, and so forth), polyolefins (such as, for example, polyethylene, polypropylene, polybutylene, polybutene, polyoctene, and so forth), polyphenylenes (such as, for example, polyphenylene oxide, polyphenylene sulfide, polyphenylene ether sulfone, and so forth), silicon containing polymers (such as, for example, polydimethyl siloxane, polycarbomethyl silane, and so forth), polyurethanes, polyvinyls (such as, for example, polyvinyl butyral, polyvinyl alcohol, esters and ethers of polyvinyl alcohol, polyvinyl acetate, polystyrene, polymethylstyrene, polyvinyl chloride, polyvinyl pyrrolidone, polymethyl vinyl ether, polyethyl vinyl ether, polyvinyl methyl ketone, and so forth), polyacetals, polyarylates, and copolymers (such as, for example, polyethylene-co-vinyl acetate, polyethylene-co-acrylic acid, polybutylene terephthalate-co-polyethylene terephthalate, polylauryllactam-block-polytetrahydrofuran, and so forth), and polylactic acid based polymers.

Useful in various embodiments of this invention are multicomponent fibers having enhanced reversible thermal properties as described in U.S. Pat. No. 6,855,422, which is hereby incorporated by reference in its entirety. These multicomponent fibers contain temperature regulating materials, generally phase change materials have the ability to absorb or release thermal energy to reduce or eliminate heat flow. In general, a phase change material may comprise any substance, or mixture of substances, that has the capability of absorbing or releasing thermal energy to reduce or eliminate heat flow at or within a temperature stabilizing range. The temperature stabilizing range may comprise a particular transition temperature or range of transition temperatures. A phase change material used in conjunction with various embodiments of the invention preferably will be capable of inhibiting a flow of thermal energy during a time when the phase change material is absorbing or releasing heat, typically as the phase change material undergoes a transition between two states, such as, for example, liquid and solid states, liquid and gaseous states, solid and gaseous states, or two solid states. This action is typically transient, and will occur until a latent heat of the phase change material is absorbed or released during a heating or cooling process. Thermal energy may be stored or removed from the phase change material, and the phase change material typically can be effectively recharged by a source of heat or cold. By selecting an appropriate phase change material, the multicomponent fiber may be designed for use in any one of numerous products.

The present invention also optionally includes a binder. Preferred binders include but are not limited to ethyl vinyl acetate copolymer such as AirFlex 124 (Air Products, Allentown, Pa.) applied at a level of about 10% solids incorporating about 0.75% by weight Aerosol OT (Cytec Industries, West Paterson, N.J.), which is an anionic surfactant. Other classes of emulsion polymer binders such as styrene-butadiene and acrylic binders may also be used. Binders AirFlex 124 and 192 (Air Products, Allentown, Pa.) having an opacifier and whitener, such as, for example, titanium dioxide, dispersed in the emulsion may also be used. Other preferred binders include but are not limited to Celanese Emulsions (Bridgewater, N.J.) Elite 22 and Elite 33. In particular embodiments where binders are used in the nonwoven material of the present invention, binders are applied in amounts ranging from about 0 to about 20 weight percent, preferably from about 0 to about 15 weight percent, more preferably from about 0 to about 8 weight percent based on the total weight of the nonwoven material.

The materials of the present invention may also include additional additives including but not limited to ultra white additives, colorants, opacity enhancers, delustrants and brighteners, and other additives to increase optical aesthetics as disclosed in U.S. patent application Ser. No. 10/707,598 filed Dec. 23, 2003, which is hereby incorporated by reference in its entirety.

In one particular embodiment of the invention, the multistrata nonwoven materials contain from about 45 to about 95 weight percent matrix fibers, which includes cellulosic fibers, synthetic fibers or a mixture thereof, and from about 5 to about 55 weight percent bicomponent fibers.

In another embodiment, the nonwoven material contains from about 0 to about 40 weight percent matrix fibers, which includes cellulosic fibers, synthetic fibers or a mixture thereof, and from about 60 to about 100 weight percent bicomponent fibers.

In another embodiment, the nonwoven material has at least one inner stratum with from about 60 to about 100 weight percent bicomponent fibers, preferably from about 70 to about 100 weight percent, more preferably from about 70 to about 95 percent, and more preferably from 75 to 95 percent bicomponent fibers based on the total weight of the inner stratum. In another embodiment, the nonwoven material has at least one inner stratum with from about 80 to about 90 weight percent bicomponent fibers. And in another embodiment, at least one inner stratum will have from about 90 to about 100 weight percent bicomponent fibers.

Methods of Producing High Strength, High Elongation Material

Various materials, structures and manufacturing processes useful in the practice of this invention are disclosed in U.S. Pat. Nos. 6,241,713; 6,353,148; 6,353,148; 6,171,441; 6,159,335; 5,695,486; 6,344,109; 5,068,079; 5,269,049; 5,693,162; 5,922,163; 6,007,653; 6,420,626, 6,355,079, 6,403,857, 6,479,415, 6,495,734, 6,562,742, 6,562,743, 6,559,081; and in U.S. patent applications with serial numbers and filing dates, Ser. No. 09/719,338 filed Jan. 17, 2001; Ser. No. 09/774,248 filed Jan. 30, 2001; and Ser. No. 09/854,179 filed May 11, 2001, all of which are hereby incorporated by reference in their entirety.

A variety of processes can be used to assemble the materials used in the practice of this invention to produce the high strength materials of this invention, including but not limited to, traditional wet laying process and dry forming processes such as airlaying and carding or other forming technologies such as spunlace or airlace. Preferably, the high strength materials can be prepared by airlaid processes. Airlaid processes include the use of one or more forming heads to deposit raw materials of differing compositions in selected order in the manufacturing process to produce a product with distinct strata. This allows great versatility in the variety of products which can be produced.

Processes and equipment useful for the production of the nonwoven material of this invention are known in the state of the art and include U.S. Pat. Nos. 4,335,066; 4,732,552; 4,375,448; 4,366,111; 4,375,447; 4,640,810; 206,632; 2,543,870; 2,588,533; 5,234,550; 4,351,793; 4,264,289; 4,666,390; 4,582,666; 5,076,774; 874,418; 5,566,611; 6,284,145; 6,363,580; 6,726,461, all of which are hereby incorporated by reference in their entirety, and of which U.S. Pat. No. 6,726,461 and U.S. Pat. No. 4,640,810 are preferred.

In one embodiment of this invention, a structure is formed with from one to six forming heads to produce material with multiple strata. The forming heads are set according to the specific target material, adding matrix fibers to the production line. The matrix fibers added to each forming head will vary depending on target material, where the matrix fibers may be cellulosic, synthetic, or a combination of cellulosic and synthetic fibers. In one embodiment, the forming head for an inner stratum produces a stratum layer comprising from about 60 to about 100 weight percent bicomponent. In another embodiment, forming head for the outer strata comprises cellulose, synthetic or a combination thereof. The higher the number of forming heads having 100% bicomponent fibers, the less synthetic material is necessary in the outer strata. The forming heads form the multistrata web which is compacted by a compaction roll. The web is then cured at temperatures approximately between 130° C.-200° C., wound and collected at a machine speed of approximately 10 meters per minute to approximately 500 meters per minute.

Various manufacturing processes of bicomponent and multicomponent fibers, and treatment of such fibers with additives, useful in the practice of this invention are disclosed in U.S. Pat. Nos. 4,394,485, 4,684,576, 4,950,541, 5,045,401, 5,082,899, 5,126,199, 5,185,199, 5,705,565, 6,855,422, 6,811,871, 6,811,716, 6,811,873, 6,838,402, 6,783,854, 6,773,810, 6,846,561, 6,841,245, 6,838,402, and 6,811,873 all of which are hereby incorporated by reference in their entirety. The ingredients are mixed, melted, cooled, and rechipped. The final chips are then incorporated into a fiber spinning process to make the desired bicomponent fiber. The rate of forming or temperatures used in the process are similar to those known in the art, for example similar to U.S. Pat. No. 4,950,541, where maleic acid or maleic compounds are integrated into bicomponent fibers, and which is incorporated herein by reference.

In one aspect of the invention, the high strength nonwoven material may be used as component of a wide variety of absorbent structures, including but not limited to wipes, diapers, feminine hygiene materials, incontinent devices, surgical drapes and associated materials, as well as mops.

EXAMPLES

The present invention will be better understood by reference to the following Examples, which are provided as exemplary of the invention, and not by way of limitation.

The airlaid pilot line used in various examples below is of either Dan-Web design and manufacture with dual drumformers and with forming heads open to the air above them, or the pilot line is of M&J design. The commercial line used for the manufacture of various examples below was of modified Dan-Web type as disclosed in U.S. Pat. No. 6,726,461, with forming heads closed to the air above them. In continuous operation, cellulose pulp sheet is fed into hammermills for comminution into individualized fibers, which are then air entrained in air flow of controlled humidity and temperature. Bicomponent fiber is then introduced into the controlled air flow on its way to the forming head, where it is mixed with the cellulose fibers in the air stream before the mixture is deposited by the forming head. For samples with non-homogeneous structures where a very high bico fiber content was deposited from a head, the same air flow system is utilized, but with little or no cellulose fiber in the flow prior to introduction of the bicomponent fiber.

In a commercial airlaid manufacturing process, it is desirable for the line speed be about 100 m/min (meters per minute) or greater, more desirably, about 200 m/min or greater, even more desirably, about 300 m/min or greater, and, preferably, about 350 m/min or greater. This is important for airlaid paper machines with a cross-machine width of about 1 meter or greater, even more important for machines with a width of about 2 meters or greater, and especially important for machines with a width of about 2.5 meters or greater.

Example 1

Homogeneous Control Samples from Pilot Line for Layered Structures

In the present Example, raw materials were combined to form pilot samples. The control materials contained a homogeneous blend of bicomponent fiber and defiberized fluff pulp in a single layer. Trevira 1661 bicomponent fiber (Bobingen, Germany), having a denier of 2.0 dpf and 6 mm fiber length, was used. The bicomponent fibers had a core made of polyester and a sheath made of polyethylene.

The structures shown in Samples 1 through 10 were prepared on a Dan-Web pilot scale airlaid manufacturing unit.

Sample 1 was prepared in one pass through the three head airlaid pilot line utilizing only one forming head. The first forming head added a mixture of 14.18 gsm of Trevira 1661 bicomponent fiber (Bobingen, Germany), having a denier of 2.0 dpf and 6 mm fiber length and 40.46 gsm of FOLEY FLUFFS® pulp (Buckeye Technologies Inc., Memphis, Tenn.). Immediately after this, the web was compacted via the compaction roll. Then the web was cured in a Moldow Through Air Tunnel Drier (Moldow Systems AS, Vaerloese, Denmark) at a temperature of temperature 145-155° C. After this the web was wound and collected. The machine speed was 10-20 meters/minute.

Samples 2 through 10 were prepared similarly to Sample 1, but with the compositions given in Table 1 and Table 2. The cross section of Samples 1-10 is shown in FIG. 3.

TABLE 1

Composition of the Pilot Samples 1-5

|  |  | 1 (gsm) | 2 (gsm) | 3 (gsm) | 4 (gsm) | 5 (gsm) |
|---|---|---|---|---|---|---|
| Single Layer | FOLEY FLUFFS ® pulp | 40.46 | 40.03 | 40.63 | 39.02 | 38.80 |
|  | Trevira 1661 bicomponent fiber | 14.18 | 13.76 | 13.28 | 13.87 | 15.45 |
|  | Total Basis Weight | 54.64 | 53.79 | 53.90 | 52.89 | 54.25 |

TABLE 2

Composition of Pilot Samples 6-10

|  |  | 6 (gsm) | 7 (gsm) | 8 (gsm) | 9 (gsm) | 10 (gsm) |
|---|---|---|---|---|---|---|
| Single Layer | FOLEY FLUFFS ® pulp | 37.35 | 36.54 | 36.14 | 46.06 | 44.88 |
|  | Trevira 1661 bicomponent fiber | 15.00 | 14.77 | 14.70 | 14.47 | 14.17 |
|  | Total Basis Weight | 52.35 | 51.31 | 50.84 | 60.53 | 59.06 |

Table 3 summarizes the performance results of all the pilot samples.

TABLE 3

Summary of the Results of Pilot Samples 1-10

| Sample # | BW (gsm) | Bicomponent Fiber % | CDW Tensile (g/in) | CDW Tensile (g/cm) |
|---|---|---|---|---|
| 1 | 54.64 | 26.0 | 421 | 166 |
| 2 | 53.79 | 25.6 | 439 | 173 |
| 3 | 53.90 | 24.6 | 392 | 154 |
| 4 | 52.89 | 26.2 | 375 | 148 |
| 5 | 54.25 | 28.5 | 473 | 186 |
| 6 | 52.35 | 28.7 | 537 | 211 |
| 7 | 51.31 | 28.8 | 608 | 239 |
| 8 | 50.84 | 28.9 | 610 | 240 |
| 9 | 60.53 | 23.9 | 494 | 194 |
| 10 | 59.06 | 24.0 | 411 | 162 |

The basis weight and cross directional wet tensile strength (CDW) were measured using the methods described earlier.

Example 2

Layered Bico Samples from Pilot Line

In the present Example, raw materials were combined to form pilot samples.

The layered materials were made of two or more layers where one or more of the layers was comprised of a layer rich in bicomponent fiber content, with a bicomponent fiber content of 60% to 100%, with a most preferred level of 100% bicomponent fiber. The other layer or layers were made of a more homogeneous blend of bicomponent fiber and defiberized fluff pulp with a bicomponent fiber content of 0% to 60%.

Trevira 1661 bicomponent fiber (Bobingen, Germany), having a denier of 2.0 dpf and 6 mm fiber length, was used. The bicomponent fibers had a core made of polyester and a sheath made of polyethylene.

The structures shown in Samples 11 through 20 were prepared on a Dan-Web pilot scale airlaid manufacturing unit.

Sample 11 was prepared in one pass through the three forming head airlaid pilot line utilizing two forming heads. The first forming head added a mixture of 7.81 gsm of Trevira 1661 bicomponent fiber (Bobingen, Germany), having a denier of 2.0 dpf and 6 mm fiber length and 40.22 gsm of FOLEY FLUFFS® pulp (Buckeye Technologies Inc., Memphis, Tenn.). The second forming head added 9.55 gsm of Trevira 1661 bicomponent fiber (Bobingen, Germany), having a denier of 2.0 dpf and 6 mm fiber length and no FOLEY FLUFFS® pulp (Buckeye Technologies Inc., Memphis, Tenn.). Immediately after this, the web was compacted via the compaction roll. Then the web was cured in a Moldow Through Air Tunnel Drier (Moldow Systems AS, Vaerloese, Denmark) at a temperature of temperature 145-155° C. After this, the web was wound and collected. The machine speed was 10-20 meters/minute.

Samples 12 through 20 were prepared similarly to Sample 11, but with the compositions given in Table 4 and Table 5. The cross section of Samples 11-20 is shown in FIG. 4.

TABLE 4

Composition of the Pilot Samples 11-15

|  |  | 11 (gsm) | 12 (gsm) | 13 (gsm) | 14 (gsm) | 15 (gsm) |
|---|---|---|---|---|---|---|
| Layer One | FOLEY FLUFFS ® pulp | 40.22 | 47.50 | 49.56 | 40.30 | 40.96 |
|  | Trevira 1661 bicomponent fiber | 7.81 | 7.17 | 7.69 | 8.07 | 5.67 |
| Layer Two | FOLEY FLUFFS ® pulp | 0 | 0 | 0 | 0 | 0 |
|  | Trevira 1661 bicomponent fiber | 9.55 | 8.76 | 9.40 | 9.87 | 6.92 |
|  | Total BW | 57.58 | 63.43 | 66.65 | 58.24 | 53.55 |

TABLE 5

Composition of Pilot Samples 16-20

|  |  | 16 (gsm) | 17 (gsm) | 18 (gsm) | 19 (gsm) | 20 (gsm) |
|---|---|---|---|---|---|---|
| Layer One | FOLEY FLUFFS ® pulp | 53.81 | 43.13 | 39.21 | 42.86 | 47.47 |
|  | Trevira 1661 bicomponent fiber | 6.29 | 6.10 | 6.87 | 6.71 | 7.88 |
| Layer Two | FOLEY FLUFFS ® pulp | 0 | 0 | 0 | 0 | 0 |
|  | Trevira 1661 bicomponent fiber | 7.69 | 7.46 | 8.40 | 8.21 | 9.63 |
|  | Total BW | 67.81 | 56.69 | 54.48 | 57.78 | 64.98 |

Table 6 summarizes the performance results of all the pilot samples.

TABLE 6

Summary of the Results of Pilot Samples 11-20

| Sample # | BW (gsm) | Bicomponent Fiber % | CDW Tensile (g/in) | CDW Tensile (g/cm) |
|---|---|---|---|---|
| 11 | 57.58 | 30.15 | 1066 | 420 |
| 12 | 63.43 | 25.11 | 751 | 296 |
| 13 | 66.65 | 25.64 | 877 | 345 |
| 14 | 58.24 | 30.81 | 1156 | 455 |
| 15 | 53.55 | 23.52 | 641 | 252 |
| 16 | 67.81 | 20.63 | 671 | 264 |
| 17 | 56.69 | 23.92 | 725 | 285 |
| 18 | 54.48 | 28.02 | 1013 | 399 |
| 19 | 57.78 | 25.82 | 929 | 366 |
| 20 | 64.98 | 26.95 | 1020 | 402 |

The data in Table 3 and Table 6 are plotted in FIG. 1. FIG. 1 shows the increase in cross directional wet (CDW) tensile strength that is achieved by using layers of 100% bicomponent fiber within a substrate versus a homogeneous blend.

Example 3

Samples from Pilot Line for Long Bico Fiber Structures and Control

In the present Example, raw materials were combined to form pilot samples.

The control materials were made of a homogeneous blend of bicomponent fiber and defiberized fluff pulp in a single layer. The structure shown in Sample 21 was prepared on a Dan-Web pilot scale airlaid manufacturing unit. Trevira 1661 bicomponent fiber (Bobingen, Germany), having a denier of 2.0 dpf and 6 mm fiber length, was used. The bicomponent fibers had a core made of polyester and a sheath made of polyethylene.

Sample 21 was prepared in one pass through the three forming head airlaid pilot line utilizing only one forming head. The first forming head added a mixture of 14.36 gsm of Trevira 1661 bicomponent fiber (Bobingen, Germany), having a denier of 2.0 dpf and 6 mm fiber length and 39.99 gsm of FOLEY FLUFFS® pulp (Buckeye Technologies Inc., Memphis, Tenn.). Immediately after this, the web was compacted via the compaction roll. Then the web was cured in a Moldow Through Air Tunnel Drier (Moldow Systems AS, Vaerloese, Denmark) at a temperature of temperature 145° C.-155° C. After this the web was wound and collected. The machine speed was 10-20 meters/minute. The composition is given in Table 7 below.

The structure shown in Sample 22 was prepared on a Dan-Web pilot scale airlaid manufacturing unit. Trevira 4178 bicomponent fiber (Bobingen, Germany), having a denier of 2.0 dpf and 12 mm fiber length, was used. The bicomponent fibers had a core made of polyester and a sheath made of polyethylene.

Sample 22 was prepared in one pass through the three forming head airlaid pilot line utilizing only one forming head. The first forming head added a mixture of 12.75 gsm of Trevira 4178 bicomponent fiber (Bobingen, Germany), having a denier of 2.0 dpf and 12 mm fiber length and 47.37 gsm of FOLEY FLUFFS® pulp (Buckeye Technologies Inc., Memphis, Tenn.). Immediately after this, the web was compacted via the compaction roll. Then the web was cured in a Moldow Through Air Tunnel Drier (Moldow Systems AS, Vaerloese, Denmark) at a temperature of temperature 145-155° C. After this the web was wound and collected. The machine speed was 10-20 meters/minute.

Samples 23 and 24 were prepared similarly to Sample 22, but with the compositions given in Table 8. The cross section of samples 21-24 is shown in FIG. 3.

TABLE 7

Composition of the Pilot Sample 21

|  |  | 21 (gsm) |
|---|---|---|
| Single Layer | FOLEY FLUFFS ® pulp | 39.99 |
|  | Trevira 1661 bicomponent fiber | 14.36 |
|  | Total BW | 54.35 |

TABLE 8

Composition of Pilot Samples 22-24

|  |  | 22 (gsm) | 23 (gsm) | 24 (gsm) |
|---|---|---|---|---|
| Single Layer | FOLEY FLUFFS ® pulp | 47.37 | 47.15 | 41.45 |
|  | Trevira 4178 bicomponent fiber | 12.75 | 16.34 | 18.45 |
|  | Total BW | 60.12 | 63.50 | 59.90 |

Table 9 summarizes the performance results of all the pilot samples.

TABLE 9

Summary of the Results of Pilot Samples 21-24

| Sample # | BW (gsm) | Bicomponent Fiber % | CDW Tensile (g/cm) | CDW Tensile (g/in) |
|---|---|---|---|---|
| 21 | 54.35 | 26.5 | 181 | 460 |
| 22 | 60.12 | 21.3 | 209 | 530 |
| 23 | 63.50 | 25.7 | 256 | 650 |
| 24 | 59.90 | 30.7 | 327 | 830 |

Figure 2:
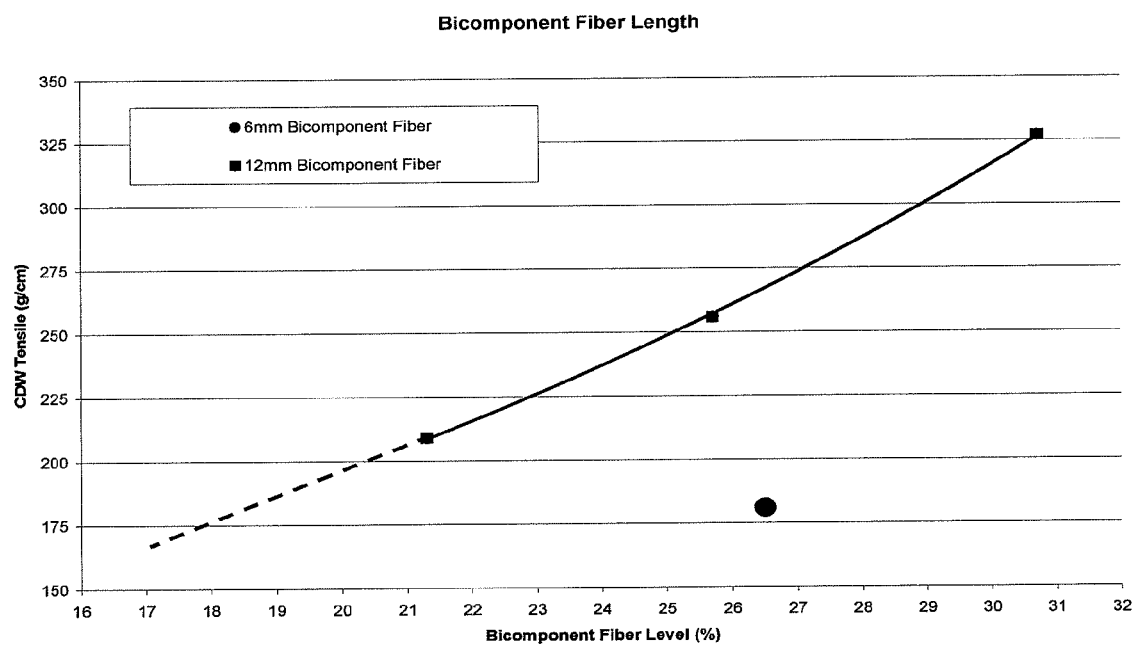
FIG. 2 depicts enhanced tensile strength of a homogenous blend of pulp and 12 mm length bicomponent fiber in CDW (g/cm) over percent of bicomponent fibers as compared to a homogenous blend of pulp and 6 mm length bicomponent fiber.

The data in Table 9 is plotted in FIG. 2. FIG. 2 shows the increase in cross directional wet (CDW) tensile strength that is achieved by using 12 mm bicomponent fiber versus 6 mm bicomponent fiber when used in a homogeneous structure.

Example 4

Samples from Commercial Line for Layered Structures and Long Fiber Structures

In the present Example, raw materials are combined to form commercial samples.

Trevira 1661 bicomponent fiber (Bobingen, Germany), having a denier of 2.0 dpf and 6 mm fiber length, is used. Trevira 4234 bicomponent fiber (Bobingen, Germany), having a denier of 1.5 dpf and 8 mm fiber length, is used. Trevira 4178 bicomponent fiber (Bobingen, Germany), having a denier of 2.0 dpf and 12 mm fiber length, is used. All of the bicomponent fibers have a core made of polyester and a sheath made of polyethylene.

The structures shown in Samples 25 through 27 are prepared in Buckeye Technologies commercial airlaid line. The cross sections of Samples 25 and 26 is shown in FIG. 5. The cross section of Sample 27 is shown in FIG. 6.

Sample 25 is prepared in one pass using five forming heads. The first forming head adds a mixture of 3.5 gsm of Trevira 1661 bicomponent fiber (Bobingen, Germany), having a denier of 2.0 dpf and 6 mm fiber length and 18.6 gsm of FOLEY FLUFFS® pulp (Buckeye Technologies Inc., Memphis, Tenn.). The second forming head adds a mixture of 10.5 gsm of Trevira 1661 bicomponent fiber (Bobingen, Germany), having a denier of 2.0 dpf and 6 mm fiber length and 9.61 gsm of FOLEY FLUFFS® pulp (Buckeye Technologies Inc., Memphis, Tenn.). The third forming head adds a mixture of 1.6 gsm of Trevira 1661 bicomponent fiber (Bobingen, Germany), having a denier of 2.0 dpf and 6 mm fiber length and 3.2 gsm of FOLEY FLUFFS® pulp (Buckeye Technologies Inc., Memphis, Tenn.). The fourth forming head adds a mixture of 1.6 gsm of Trevira 1661 bicomponent fiber (Bobingen, Germany), having a denier of 2.0 dpf and 6 mm fiber length and 3.2 gsm of FOLEY FLUFFS® pulp (Buckeye Technologies Inc., Memphis, Tenn.). The fifth forming head adds a mixture of 1.2 gsm of Trevira 1661 bicomponent fiber (Bobingen, Germany), having a denier of 2.0 dpf and 6 mm fiber length and 5.0 gsm of FOLEY FLUFFS® pulp (Buckeye Technologies Inc., Memphis, Tenn.). Immediately after this, the web is compacted via the compaction roll. Then the web is sprayed with 1.6 gsm of Airflex 192 ethylvinylacetate binder (Air Products, Allentown, Pa.) solids in the form of an aqueous emulsion and cured in a through air oven. The web is then sprayed again with 1.0 gsm of Airflex 192 binder (Air Products, Allentown, Pa.) solids in the form of an aqueous emulsion and is cured in a second through air oven. Both ovens are at a temperature between 135-195° C. After this, the web is wound and is collected. The composition is given in Table 10.

Samples 26 and 27 are prepared similarly to Sample 25, but with the compositions given in Tables 11 and 12.

TABLE 10

Composition of the Commercial Sample 25

|  |  | 25 (gsm) |
|---|---|---|
| Top Binder | Air Products AF192 binder | 1.6 |
| Layer One | FOLEY FLUFFS ® pulp | 18.6 |
|  | Trevira 1661 bicomponent fiber | 3.5 |
| Layer Two | FOLEY FLUFFS ® pulp | 9.6 |
|  | Trevira 1661 bicomponent fiber | 10.5 |
| Layer Three | FOLEY FLUFFS ® pulp | 3.2 |
|  | Trevira 1661 bicomponent fiber | 1.6 |
| Layer Four | FOLEY FLUFFS ® pulp | 3.2 |
|  | Trevira 1661 bicomponent fiber | 1.6 |
| Layer Five | FOLEY FLUFFS ® pulp | 5.0 |
|  | Trevira 1661 bicomponent fiber | 1.2 |
| Bottom Binder | Air Products AF192 binder | 1.0 |
|  | Total BW | 60.6 |

TABLE 11

Composition of the Commercial Sample 26

|  |  | 26 (gsm) |
|---|---|---|
| Top Binder | Air Products AF192 binder | 1.4 |
| Layer One | FOLEY FLUFFS ® pulp | 18.2 |
|  | Trevira 1661 bicomponent fiber | 4.6 |
| Layer Two | FOLEY FLUFFS ® pulp | 9.1 |
|  | Trevira 4234 bicomponent fiber | 9.9 |
| Layer Three | FOLEY FLUFFS ® pulp | 2.6 |
|  | Trevira 1661 bicomponent fiber | 1.4 |
| Layer Four | FOLEY FLUFFS ® pulp | 2.6 |
|  | Trevira 1661 bicomponent fiber | 1.4 |
| Layer Five | FOLEY FLUFFS ® pulp | 4.5 |
|  | Trevira 1661 bicomponent fiber | 1.3 |
| Bottom Binder | Air Products AF192 binder | 1.0 |
|  | Total BW | 58.0 |

TABLE 12

Composition of the Commercial Sample 27

|  |  | 27 (gsm) |
|---|---|---|
| Top Binder | Air Products AF192 binder | 2.0 |
| Layer One | FOLEY FLUFFS ® pulp | 22.9 |
|  | Trevira 1661 bicomponent fiber | 6.1 |
| Layer Two | FOLEY FLUFFS ® pulp | 0 |
|  | Trevira 4178 bicomponent fiber | 6.5 |
| Layer | FOLEY FLUFFS ® pulp | 4.3 |

TABLE 12-continued

Composition of the Commercial Sample 27

| | | 27 (gsm) |
|---|---|---|
| Three | Trevira 1661 bicomponent fiber | 1.7 |
| Layer | FOLEY FLUFFS ® pulp | 4.1 |
| Four | Trevira 1661 bicomponent fiber | 1.7 |
| Layer | FOLEY FLUFFS ® pulp | 6.4 |
| Five | Trevira 1661 bicomponent fiber | 1.5 |
| Bottom Binder | Air Products AF192 binder | 1.2 |
| | Total BW | 58.4 |

Example 4B

Samples from Commercial Line for Layered Structures and Long Fiber Structures

In the present Example, raw materials were combined to form samples on a commercial drum forming line.

Trevira 1661 bicomponent fiber (Bobingen, Germany), having a denier of 2.0 dpf and 6 mm fiber length, was used. Trevira 4234 bicomponent fiber (Bobingen, Germany), having a denier of 1.5 dpf and 8 mm fiber length, was used. Trevira 4178 bicomponent fiber (Bobingen, Germany), having a denier of 2.0 dpf and 12 mm fiber length, was used. Invista T255 bicomponent fiber (Salisbury, N.C.), having a denier of 2.0 dpf and 6 mm fiber length was used. All of the bicomponent fibers had a core made of polyester and a sheath made of polyethylene.

The structures shown in Samples 25B through 27B were prepared in Buckeye Technologies commercial airlaid line. The cross sections of Samples 25B and 26B is shown in FIG. 5. The cross section of Sample 27B is shown in FIG. 6.

Sample 25B was prepared in one pass using five forming heads. The first forming head added a mixture of 3.5 gsm of Trevira 1661 bicomponent fiber (Bobingen, Germany), having a denier of 2.0 dpf and 6 mm fiber length and 18.6 gsm of FOLEY FLUFFS® pulp (Buckeye Technologies Inc., Memphis, Tenn.). The second forming head added a mixture of 10.5 gsm of Invista T255 bicomponent fiber (Salisbury, N.C.), having a denier of 2.0 dpf and 6 mm fiber length and 9.61 gsm of FOLEY FLUFFS® pulp (Buckeye Technologies Inc., Memphis, Tenn.). The third forming head added a mixture of 1.6 gsm of Invista T255 bicomponent fiber (Salisbury, N.C.), having a denier of 2.0 dpf and 6 mm fiber length and 3.2 gsm of FOLEY FLUFFS®(T pulp (Buckeye Technologies Inc., Memphis, Tenn.). The fourth forming head added a mixture of 1.6 gsm of Invista T255 bicomponent fiber (Salisbury, N.C.), having a denier of 2.0 dpf and 6 mm fiber length and 3.2 gsm of FOLEY FLUFFS® pulp (Buckeye Technologies Inc., Memphis, Tenn.). The fifth forming head added a mixture of 1.2 gsm of Invista T255 bicomponent fiber (Salisbury, N.C.), having a denier of 2.0 dpf and 6 mm fiber length and 5.0 gsm of FOLEY FLUFFS® pulp (Buckeye Technologies Inc., Memphis, Tenn.). Immediately after this, the web was compacted via the compaction roll. Then the web was sprayed with 1.6 gsm of Airflex 124 ethylvinylacetate binder (Air Products, Allentown, Pa.) solids in the form of an aqueous emulsion and cured in a through air oven. Then the web was then sprayed again with 1.0 gsm of Airflex 124 binder (Air Products, Allentown, Pa.) solids in the form of an aqueous emulsion and cured in a second through air oven. Both ovens were at a temperature between 135-195° C. After this the web was wound and collected. The composition is given in Table 10B.

Samples 26B and 27B were prepared similarly to Sample 25B, but with the compositions given in Tables 11B and 12B.

TABLE 10B

Composition of the Commercial Sample 25B

| | | 25 (gsm) |
|---|---|---|
| Top Binder | Air Products AF124 binder | 1.6 |
| Layer | FOLEY FLUFFS ® pulp | 18.6 |
| One | Trevira 1661 bicomponent fiber | 3.5 |
| Layer | FOLEY FLUFFS ® pulp | 9.6 |
| Two | Invista T255 bicomponent fiber | 10.5 |
| Layer | FOLEY FLUFFS ® pulp | 3.2 |
| Three | Invista T255 bicomponent fiber | 1.6 |
| Layer | FOLEY FLUFFS ® pulp | 3.2 |
| Four | Invista T255 bicomponent fiber | 1.6 |
| Layer | FOLEY FLUFFS ® pulp | 5.0 |
| Five | Invista T255 bicomponent fiber | 1.2 |
| Bottom Binder | Air Products AF124 binder | 1.0 |
| | Total BW | 60.6 |

TABLE 11B

Composition of the Commercial Sample 26B

| | | 26 (gsm) |
|---|---|---|
| Top Binder | Air Products AF124binder | 1.4 |
| Layer | FOLEY FLUFFS ® pulp | 18.2 |
| One | Trevira 1661 bicomponent fiber | 4.6 |
| Layer | FOLEY FLUFFS ® pulp | 9.1 |
| Two | Trevira 4234 bicomponent fiber | 9.9 |
| Layer | FOLEY FLUFFS ® pulp | 2.6 |
| Three | Invista T255 bicomponent fiber | 1.4 |
| Layer | FOLEY FLUFFS ® pulp | 2.6 |
| Four | Invista T255 bicomponent fiber | 1.4 |
| Layer | FOLEY FLUFFS ® pulp | 4.5 |
| Five | Invista T255 bicomponent fiber | 1.3 |
| Bottom Binder | Air Products AF124 binder | 1.0 |
| | Total BW | 58.0 |

TABLE 12B

Composition of the Commercial Sample 27B

| | | 27 (gsm) |
|---|---|---|
| Top Binder | Air Products AF124binder | 2.0 |
| Layer | FOLEY FLUFFS ® pulp | 22.9 |
| One | Trevira 1661 bicomponent fiber | 6.1 |
| Layer | FOLEY FLUFFS ® pulp | 0 |
| Two | Trevira 4178 bicomponent fiber | 6.5 |
| Layer | FOLEY FLUFFS ® pulp | 4.3 |
| Three | Invista T255 bicomponent fiber | 1.7 |
| Layer | FOLEY FLUFFS ® pulp | 4.1 |
| Four | Invista T255 bicomponent fiber | 1.7 |
| Layer | FOLEY FLUFFS ® pulp | 6.4 |
| Five | Invista T255 bicomponent fiber | 1.5 |
| Bottom Binder | Air Products AF124 binder | 1.2 |
| | Total BW | 58.4 |

Table 13B summarizes the performance results of all the pilot samples.

TABLE 13B

Summary of the Results of Commercial Samples 25B-27B

| Sample # | BW (gsm) | Bicomponent Fiber % | CDW Tensile (g/in) | CDW Tensile (g/cm) |
|---|---|---|---|---|
| 25B | 60.6 | 30.1 | 585 | 230 |
| 26B | 58.0 | 29.9 | 675 | 266 |
| 27B | 58.4 | 29.7 | 736 | 290 |

A comparison of Sample 25B to Sample 26B shows that the 8 mm cut length bico fiber in the second layer of Sample 26B provides higher CDW strength than the 6 mm cut length bico fiber in the second layer of Sample 25B, with the rest of the structure nominally the same.

A comparison of Sample 27B to Sample 25B shows that the 100% layer of 12 mm bico fiber in the second layer provides significantly higher CDW strength than the 6 mm bico fiber, fluff pulp blend layer of Sample 25B even though Sample 25B has an overall higher level of bicomponent fiber.

Example 5

Samples from Pilot Line for Partially Drawn Core Bicomponent Fibers Structures and Layered Structures In the present Example, raw materials were combined to form pilot samples.

The structure shown in Sample 28 was prepared on a Dan-Web pilot scale airlaid manufacturing unit. Trevira T265 bicomponent fiber (Bobingen, Germany), having a denier of 2.0 dpf and 6 mm fiber length, and a partially drawn core was used. This bicomponent fiber had a core made of polybutylene terephthalate (PBT) and a sheath made of polyethylene. Trevira 1661 bicomponent fiber (Bobingen, Germany), having a denier of 2.0 dpf and 6 mm fiber length was also used. This bicomponent fiber has a polyester core and a polyethylene sheath.

Sample 28 was prepared in one pass through the three forming head airlaid pilot line utilizing three forming heads. The first forming head added a mixture of 7.79 gsm of Trevira 1661 bicomponent fiber (Bobingen, Germany), having a denier of 2.0 dpf and 6 mm fiber length and 20.84 gsm of FOLEY FLUFFS® pulp (Buckeye Technologies Inc., Memphis, Tenn.). The second forming head added 12.47 gsm of Trevira T265 bicomponent fiber (Bobingen, Germany), having a denier of 2.0 dpf and 6 mm fiber length with a partially drawn core. The third forming head added a mixture of 7.79 gsm of Trevira 1661 bicomponent fiber (Bobingen, Germany), having a denier of 2.0 dpf and 6 mm fiber length and 20.84 gsm of FOLEY FLUFFS® pulp (Buckeye Technologies Inc., Memphis, Tenn.). Immediately after this, the web was compacted via the compaction roll. Then the web was cured in a Moldow Through Air Tunnel Drier (Moldow Systems AS, Vaerloese, Denmark) at a temperature of temperature 145-155° C. After this the web was wound and collected. The machine speed was 10-20 meters/minute. The composition is given in Table 14 below.

Samples 29 and 30 were prepared similarly to Sample 28, but with the compositions given in Table 15 and Table 16. The cross-section of Sample 28 is shown in FIG. 6. The cross section of Sample 29 is shown in FIG. 5, and the cross-section of Sample 30 is shown in FIG. 3.

TABLE 14

Composition of the Pilot Sample 28

|  |  | 28 (gsm) |
|---|---|---|
| Layer One | FOLEY FLUFFS ® pulp | 20.84 |
|  | Trevira 1661 bicomponent fiber | 7.79 |
| Layer Two | FOLEY FLUFFS ® pulp | 0 |
|  | Trevira T265 partially drawn core bicomponent fiber | 12.47 |
| Layer Three | FOLEY FLUFFS ® pulp | 20.84 |
|  | Trevira 1661 bicomponent fiber | 7.79 |
|  | Total BW | 69.73 |

TABLE 15

Composition of the Pilot Sample 29

|  |  | 29 (gsm) |
|---|---|---|
| Layer One | FOLEY FLUFFS ® pulp | 19.52 |
|  | Trevira 1661 bicomponent fiber | 8.66 |
| Layer Two | FOLEY FLUFFS ® pulp | 4.44 |
|  | Trevira T265 partially drawn core bicomponent fiber | 13.86 |
| Layer Three | FOLEY FLUFFS ® pulp | 15.08 |
|  | Trevira 1661 bicomponent fiber | 8.66 |
|  | Total BW | 70.22 |

TABLE 16

Composition of the Pilot Sample 30

|  |  | 30 (gsm) |
|---|---|---|
| Single Layer | FOLEY FLUFFS ® pulp | 55.17 |
|  | Trevira T265 partially drawn core bicomponent fiber | 18.65 |
|  | Total BW | 73.82 |

Table 17 summarizes the performance results of all the pilot samples.

TABLE 17

Summary of the Results of Pilot Samples 28-30

| Sample # | BW (gsm) | Bicomponent Fiber % | CDW Tensile (g/in) | CDW Tensile (g/cm) | CDW Elongation (%) |
|---|---|---|---|---|---|
| 28 | 69.73 | 40.2 | 1446 | 569 | 44.6 |
| 29 | 70.22 | 44.4 | 1730 | 681 | 43.8 |
| 30 | 73.82 | 25.3 | 780 | 307 | 41.4 |

The structure shown in Sample 31 was prepared on a Dan-Web pilot scale airlaid manufacturing unit. Trevira T255 bicomponent fiber (Bobingen, Germany), having a denier of 4.0 dpf and 6 mm fiber length, and a partially drawn core was used. This bicomponent fiber had a core made of polyester and a sheath made of polyethylene. Trevira 1661 bicomponent fiber (Bobingen, Germany), having a denier of 2.0 dpf and 6 mm fiber length was also used. This bicomponent fiber has a polyester core and a polyethylene sheath.

Sample 31 was prepared in one pass through the three forming head airlaid pilot line utilizing three forming heads.

The first forming head added a mixture of 6.51 gsm of Trevira 1661 bicomponent fiber (Bobingen, Germany), having a denier of 2.0 dpf and 6 mm fiber length and 19.81 gsm of FOLEY FLUFFS® pulp (Buckeye Technologies Inc., Memphis, Tenn.). The second forming head added 10.43 gsm of Trevira T255 bicomponent fiber (Bobingen, Germany), having a denier of 4.0 dpf and 6 mm fiber length with a partially drawn core. The third forming head added a mixture of 6.51 gsm of Trevira 1661 bicomponent fiber (Bobingen, Germany), having a denier of 2.0 dpf and 6 mm fiber length and 19.81 gsm of FOLEY FLUFFS® pulp (Buckeye Technologies Inc., Memphis, Tenn.). Immediately after this, the web was compacted via the compaction roll. Then the web was cured in a Moldow Through Air Tunnel Drier (Moldow Systems AS, Vaerloese, Denmark) at a temperature of temperature 145-155° C. After this the web was wound and collected. The machine speed was 10-20 meters/minute. The composition is given in Table 18 below.

Samples 32 and 33 were prepared similarly to Sample 31, but with the compositions given in Table 19 and Table 20. The cross section of Sample 31 is shown in FIG. 6, the cross section of Sample 32 is shown in FIG. 5 and the cross section of Sample 33 is shown in FIG. 3.

TABLE 18

Composition of the Pilot Sample 31

|   |   | 31 (gsm) |
|---|---|---|
| Layer One | FOLEY FLUFFS ® pulp | 19.81 |
|  | Trevira 1661 bicomponent fiber | 6.51 |
| Layer Two | FOLEY FLUFFS ® pulp | 0 |
|  | Trevira T255 4.0 dpf partially drawn core bicomponent fiber | 10.43 |
| Layer Three | FOLEY FLUFFS ® pulp | 19.81 |
|  | Trevira 1661 bicomponent fiber | 6.51 |
|  | Total BW | 63.07 |

TABLE 19

Composition of the Pilot Sample 32

|   |   | 32 (gsm) |
|---|---|---|
| Layer One | FOLEY FLUFFS ® pulp | 19.26 |
|  | Trevira 1661 bicomponent fiber | 6.65 |
| Layer Two | FOLEY FLUFFS ® pulp | 4.38 |
|  | Trevira T255 4.0 dpf partially drawn core bicomponent fiber | 10.63 |
| Layer Three | FOLEY FLUFFS ® pulp | 14.88 |
|  | Trevira 1661 bicomponent fiber | 6.65 |
|  | Total BW | 62.45 |

TABLE 20

Composition of the Pilot Sample 33

|   |   | 33 (gsm) |
|---|---|---|
| Single Layer | FOLEY FLUFFS ® pulp | 54.13 |
|  | Trevira T255 4.0 dpf partially drawn core bicomponent fiber | 15.92 |
|  | Total BW | 70.05 |

Table 21 summarizes the performance results of all the pilot samples.

TABLE 21

Summary of the Results of Pilot Samples 31-33

| Sample # | BW (gsm) | Bicomponent Fiber % | CDW Tensile (g/in) | CDW Tensile (g/cm) | CDW Elongation (%) |
|---|---|---|---|---|---|
| 31 | 63.07 | 37.17 | 944 | 372 | 40.6 |
| 32 | 62.45 | 38.31 | 961 | 378 | 37.6 |
| 33 | 70.05 | 22.72 | 423 | 167 | 33.6 |

The structure shown in Sample 34 was prepared on a Dan-Web pilot scale airlaid manufacturing unit. Trevira T255 bicomponent fiber (Bobingen, Germany), having a denier of 2.0 dpf and 6 mm fiber length, and a partially drawn core was used. This bicomponent fiber had a core made of polyester and a sheath made of polyethylene. Trevira 1661 bicomponent fiber (Bobingen, Germany), having a denier of 2.0 dpf and 6 mm fiber length was also used. This bicomponent fiber has a polyester core and a polyethylene sheath.

Sample 34 was prepared in one pass through the three forming head airlaid pilot line utilizing three forming heads. The first forming head added a mixture of 7.31 gsm of Trevira 1661 bicomponent fiber (Bobingen, Germany), having a denier of 2.0 dpf and 6 mm fiber length and 19.30 gsm of FOLEY FLUFFS® pulp (Buckeye Technologies Inc., Memphis, Tenn.). The second forming head added 11.71 gsm of Trevira T255 bicomponent fiber (Bobingen, Germany), having a denier of 2.0 dpf and 6 mm fiber length with a partially drawn core. The third forming head added a mixture of 7.31 gsm of Trevira 1661 bicomponent fiber (Bobingen, Germany), having a denier of 2.0 dpf and 6 mm fiber length and 19.30 gsm of FOLEY FLUFFS® pulp (Buckeye Technologies Inc., Memphis, Tenn.). Immediately after this, the web was compacted via the compaction roll. Then the web was cured in a Moldow Through Air Tunnel Drier (Moldow Systems AS, Vaerloese, Denmark) at a temperature of temperature 145-155° C. After this the web was wound and collected. The machine speed was 10-20 meters/minute. The composition is given in Table 22 below.

Samples 35 and 36 were prepared similarly to Sample 34, but with the compositions given in Table 23 and Table 24. The cross section of Sample 34 is shown in FIG. 6, the cross section of Sample 35 is shown in FIG. 5 and the cross section of Sample 36 is shown in FIG. 3.

TABLE 22

Composition of the Pilot Sample 34

|   |   | 34 (gsm) |
|---|---|---|
| Layer One | FOLEY FLUFFS ® pulp | 19.30 |
|  | Trevira 1661 bicomponent fiber | 7.31 |
| Layer Two | FOLEY FLUFFS ® pulp | 0 |
|  | Trevira T255 2.0 dpf partially drawn core bicomponent fiber | 11.71 |
| Layer Three | FOLEY FLUFFS ® pulp | 19.30 |
|  | Trevira 1661 bicomponent fiber | 7.31 |
|  | Total BW | 64.93 |

TABLE 23

Composition of the Pilot Sample 35

|  |  | 35 (gsm) |
|---|---|---|
| Layer One | FOLEY FLUFFS ® pulp | 20.34 |
|  | Trevira 1661 bicomponent fiber | 8.61 |
| Layer Two | FOLEY FLUFFS ® pulp | 4.63 |
|  | Trevira T255 2.0 dpf partially drawn core bicomponent fiber | 13.78 |
| Layer Three | FOLEY FLUFFS ® pulp | 15.72 |
|  | Trevira 1661 bicomponent fiber | 8.61 |
|  | Total BW | 71.69 |

TABLE 24

Composition of the Pilot Sample 36

|  |  | 33 (gsm) |
|---|---|---|
| Single Layer | FOLEY FLUFFS ® pulp | 49.64 |
|  | Trevira T255 2.0 dpf partially drawn core bicomponent fiber | 17.33 |
|  | Total BW | 66.97 |

Table 25 summarizes the performance results of all the pilot samples.

TABLE 25

Summary of the Results of Pilot Samples 34-36

| Sample # | BW (gsm) | Bicomponent Fiber % | CDW Tensile (g/in) | CDW Tensile (g/cm) | CDW Elongation (%) |
|---|---|---|---|---|---|
| 34 | 64.93 | 40.6 | 1028 | 405 | 39.0 |
| 35 | 71.69 | 43.2 | 1502 | 591 | 40.4 |
| 36 | 66.97 | 25.9 | 535 | 211 | 35.3 |

The structure shown in Sample 37 was prepared on a Dan-Web pilot scale airlaid manufacturing unit. Trevira 1661 bicomponent fiber (Bobingen, Germany), having a denier of 2.0 dpf and 6 mm fiber length was used. This bicomponent fiber has a polyester core and a polyethylene sheath.

Sample 37 was prepared in one pass through the three forming head airlaid pilot line utilizing three forming heads. The first forming head added a mixture of 9.06 gsm of Trevira 1661 bicomponent fiber (Bobingen, Germany), having a denier of 2.0 dpf and 6 mm fiber length and 15.58 gsm of FOLEY FLUFFS®(pulp (Buckeye Technologies Inc., Memphis, Tenn.). The second forming head added 14.48 gsm of Trevira 1661 bicomponent fiber (Bobingen, Germany), having a denier of 2.0 dpf and 6 mm fiber length. The third forming head added a mixture of 9.06 gsm of Trevira 1661 bicomponent fiber (Bobingen, Germany), having a denier of 2.0 dpf and 6 mm fiber length and 15.58 gsm of FOLEY FLUFFS® pulp (Buckeye Technologies Inc., Memphis, Tenn.). Immediately after this, the web was compacted via the compaction roll. Then the web was cured in a Moldow Through Air Tunnel Drier (Moldow Systems AS, Vaerloese, Denmark) at a temperature of temperature 145-155° C. After this the web was wound and collected. The machine speed was 10-20 meters/minute. The composition is given in Table 26 below.

Samples 38 and 39 were prepared similarly to Sample 37, but with the compositions given in Table 27 and Table 28. The cross section of Sample 37 is shown in FIG. 6, the cross section of Sample 38 is shown in FIG. 5 and the cross section of Sample 39 is shown in FIG. 3.

TABLE 26

Composition of the Pilot Sample 37

|  |  | 37 (gsm) |
|---|---|---|
| Layer One | FOLEY FLUFFS ® pulp | 15.58 |
|  | Trevira 1661 bicomponent fiber | 9.06 |
| Layer Two | FOLEY FLUFFS ® pulp | 0 |
|  | Trevira 1661 bicomponent fiber | 14.48 |
| Layer Three | FOLEY FLUFFS ® pulp | 15.58 |
|  | Trevira 1661 bicomponent fiber | 9.06 |
|  | Total BW | 63.76 |

TABLE 27

Composition of the Pilot Sample 38

|  |  | 38 (gsm) |
|---|---|---|
| Layer One | FOLEY FLUFFS ® pulp | 19.63 |
|  | Trevira 1661 bicomponent fiber | 6.73 |
| Layer Two | FOLEY FLUFFS ® pulp | 4.46 |
|  | Trevira 1661 bicomponent fiber | 10.75 |
| Layer Three | FOLEY FLUFFS ® pulp | 15.17 |
|  | Trevira 1661 bicomponent fiber | 6.73 |
|  | Total BW | 63.47 |

TABLE 28

Composition of the Pilot Sample 39

|  |  | 39 (gsm) |
|---|---|---|
| Single Layer | FOLEY FLUFFS ® pulp | 43.21 |
|  | Trevira 1661 bicomponent fiber | 11.64 |
|  | Total BW | 54.85 |

Table 29 summarizes the performance results of all the pilot samples.

TABLE 29

Summary of the Results of Pilot Samples 37-39

| Sample # | BW (gsm) | Bicomponent Fiber % | CDW Tensile (g/in) | CDW Tensile (g/cm) | CDW Elongation (%) |
|---|---|---|---|---|---|
| 37 | 63.76 | 51.14 | 1135 | 447 | 33.5 |
| 38 | 63.47 | 38.15 | 894 | 352 | 32.3 |
| 39 | 54.85 | 21.22 | 317 | 125 | 28.6 |

The structure shown in Sample 40 was prepared on a Dan-Web pilot scale airlaid manufacturing unit. Trevira T255 bicomponent fiber (Bobingen, Germany), having a denier of 2.0 dpf and 6 mm fiber length, and a partially drawn core was used. This bicomponent fiber had a core made of polyester and a sheath made of polyethylene. Trevira 1661 bicomponent fiber (Bobingen, Germany), having a denier of 2.0 dpf and 6 mm fiber length was also used. This bicomponent fiber has a polyester core and a polyethylene sheath.

Sample 40 was prepared in one pass through the three forming head airlaid pilot line utilizing three forming heads. The first forming head added a mixture of 4.99 gsm of Trevira 1661 bicomponent fiber (Bobingen, Germany), having a denier of 2.0 dpf and 6 mm fiber length and 18.32 gsm of FOLEY FLUFFS® pulp (Buckeye Technologies Inc., Memphis, Tenn.). The second forming head added 7.99 gsm of Trevira T255 bicomponent fiber (Bobingen, Germany), having a denier of 2.0 dpf and 6 mm fiber length with a partially drawn core. The third forming head added a mixture of 4.99 gsm of Trevira 1661 bicomponent fiber (Bobingen, Germany), having a denier of 2.0 dpf and 6 mm fiber length and 18.32 gsm of FOLEY FLUFFS® pulp (Buckeye Technologies Inc., Memphis, Tenn.). Immediately after this, the web was compacted via the compaction roll. Then the web was cured in a Moldow Through Air Tunnel Drier (Moldow Systems AS, Vaerloese, Denmark) at a temperature of temperature 145-155° C. After this the web was wound and collected. The machine speed was 10-20 meters/minute. The composition is given in Table 30 below.

Samples 41 and 42 were prepared similarly to Sample 40, but with the compositions given in Table 31 and Table 32. The cross section of Sample 40 is shown in FIG. 6, the cross section of Sample 41 is shown in FIG. 5 and the cross section of Sample 42 is shown in FIG. 5.

TABLE 30

Composition of the Pilot Sample 40

|  |  | 40 (gsm) |
|---|---|---|
| Layer One | FOLEY FLUFFS ® pulp | 18.32 |
|  | Trevira 1661 bicomponent fiber | 4.99 |
| Layer Two | FOLEY FLUFFS ® pulp | 0 |
|  | Trevira T255 2.0 dpf partially drawn core bicomponent fiber | 7.99 |
| Layer Three | FOLEY FLUFFS ® pulp | 18.32 |
|  | Trevira 1661 bicomponent fiber | 4.99 |
|  | Total BW | 54.61 |

TABLE 31

Composition of the Pilot Sample 41

|  |  | 41 (gsm) |
|---|---|---|
| Layer One | FOLEY FLUFFS ® pulp | 20.70 |
|  | Trevira 1661 bicomponent fiber | 6.73 |
| Layer Two | FOLEY FLUFFS ® pulp | 1.88 |
|  | Trevira T255 2.0 dpf partially drawn core bicomponent fiber | 10.77 |
| Layer Three | FOLEY FLUFFS ® pulp | 18.82 |
|  | Trevira 1661 bicomponent fiber | 6.73 |
|  | Total BW | 65.63 |

TABLE 32

Composition of the Pilot Sample 42

|  |  | 42 (gsm) |
|---|---|---|
| Layer One | FOLEY FLUFFS ® pulp | 18.70 |
|  | Trevira 1661 bicomponent fiber | 5.41 |
| Layer | FOLEY FLUFFS ® pulp | 4.25 |

TABLE 32-continued

Composition of the Pilot Sample 42

|  |  | 42 (gsm) |
|---|---|---|
| Two | Trevira T255 2.0 dpf partially drawn core bicomponent fiber | 8.65 |
| Layer Three | FOLEY FLUFFS ® pulp | 14.45 |
|  | Trevira 1661 bicomponent fiber | 5.41 |
|  | Total BW | 56.87 |

Table 33 summarizes the performance results of all the pilot samples.

TABLE 33

Summary of the Results of Pilot Samples 40-42

| Sample # | BW (gsm) | Bicomponent Fiber % | CDW Tensile (g/in) | CDW Tensile (g/cm) | CDW Elongation (%) |
|---|---|---|---|---|---|
| 40 | 54.61 | 32.91 | 1027 | 404 | 50.5 |
| 41 | 65.63 | 36.92 | 1567 | 617 | 54.1 |
| 42 | 56.87 | 34.24 | 896 | 353 | 43.4 |

The structure shown in Sample 43 was prepared on a Dan-Web pilot scale airlaid manufacturing unit. Trevira 1661 bicomponent fiber (Bobingen, Germany), having a denier of 2.0 dpf and 6 mm fiber length was used. This bicomponent fiber has a polyester core and a polyethylene sheath.

Sample 43 was prepared in one pass through the three forming head airlaid pilot line utilizing three forming heads. The first forming head added a mixture of 5.38 gsm of Trevira 1661 bicomponent fiber (Bobingen, Germany), having a denier of 2.0 dpf and 6 mm fiber length and 19.96 gsm of FOLEY FLUFFS® pulp (Buckeye Technologies Inc., Memphis, Tenn.). The second forming head added 8.61 gsm of Trevira 1661 bicomponent fiber (Bobingen, Germany), having a denier of 2.0 dpf and 6 mm fiber length. The third forming head added a mixture of 5.38 gsm of Trevira 1661 bicomponent fiber (Bobingen, Germany), having a denier of 2.0 dpf and 6 mm fiber length and 19.96 gsm of FOLEY FLUFFS® pulp (Buckeye Technologies Inc., Memphis, Tenn.). Immediately after this, the web was compacted via the compaction roll. Then the web was cured in a Moldow Through Air Tunnel Drier (Moldow Systems AS, Vaerloese, Denmark) at a temperature of temperature 145-155° C. After this the web was wound and collected. The machine speed was 10-20 meters/minute. The composition is given in Table 34 below.

Samples 44 and 45 were prepared similarly to Sample 43, but with the compositions given in Table 35 and Table 36. The cross section of Sample 32 is shown in FIG. 6, the cross section of Sample 44 is shown in FIG. 5 and the cross section of Sample 45 is shown in FIG. 5.

TABLE 34

Composition of the Pilot Sample 43

|  |  | 43 (gsm) |
|---|---|---|
| Layer One | FOLEY FLUFFS ® pulp | 19.96 |
|  | Trevira 1661 bicomponent fiber | 5.38 |
| Layer | FOLEY FLUFFS ® pulp | 0 |

TABLE 34-continued

Composition of the Pilot Sample 43

|  |  | 43 (gsm) |
|---|---|---|
| Two Layer | Trevira 1661 bicomponent fiber | 8.61 |
| Three | FOLEY FLUFFS ® pulp | 19.96 |
|  | Trevira 1661 bicomponent fiber | 5.38 |
|  | Total BW | 59.29 |

TABLE 35

Composition of the Pilot Sample 44

|  |  | 44 (gsm) |
|---|---|---|
| Layer One | FOLEY FLUFFS ® pulp | 24.48 |
|  | Trevira 1661 bicomponent fiber | 6.18 |
| Layer Two | FOLEY FLUFFS ® pulp | 2.23 |
|  | Trevira 1661 bicomponent fiber | 9.88 |
| Layer Three | FOLEY FLUFFS ® pulp | 22.25 |
|  | Trevira 1661 bicomponent fiber | 6.18 |
|  | Total BW | 71.20 |

TABLE 36

Composition of the Pilot Sample 45

|  |  | 45 (gsm) |
|---|---|---|
| Layer One | FOLEY FLUFFS ® pulp | 18.81 |
|  | Trevira 1661 bicomponent fiber | 4.29 |
| Layer Two | FOLEY FLUFFS ® pulp | 4.27 |
|  | Trevira 1661 bicomponent fiber | 6.86 |
| Layer Three | FOLEY FLUFFS ® pulp | 14.53 |
|  | Trevira 1661 bicomponent fiber | 4.29 |
|  | Total BW | 53.05 |

Table 37 summarizes the performance results of all the pilot samples.

TABLE 37

Summary of the Results of Pilot Samples 43-45

| Sample # | BW (gsm) | Bicomponent Fiber % | CDW Tensile (g/in) | CDW Tensile (g/cm) | CDW Elongation (%) |
|---|---|---|---|---|---|
| 43 | 59.29 | 32.66 | 1056 | 416 | 35.7 |
| 44 | 71.20 | 31.23 | 927 | 365 | 36.0 |
| 45 | 53.05 | 29.10 | 559 | 220 | 33.9 |

All of the following comparisons take into account the various levels of bicomponent fiber, pulp and basis weight variations. A comparison of Samples 37, 38 & 39 using commercial Trevira 1661 bicomponent fiber versus Samples 28 to 36 that used partially drawn core bicomponent fibers shows that using a partially drawn core bicomponent fiber delivers higher wet elongation and higher wet tensile strength even as core polymer and denier are varied. A comparison of Samples 43-45 versus Samples 40-42 shows that a partially drawn PET core bicomponent fiber gives higher strength and elongation than a commercial Trevira 1661 bicomponent fiber of the same denier and cut length. A comparison of Samples 43, 44 and 45 to each other shows that increasing the percentage of commercial Trevira 1661 bicomponent fiber in the middle layer from 60% to 80% and finally to 100% increases the wet tensile strength, but has minimal impact on the wet elongation. A level of 100% Trevira 1661 at 2.0 dpf and 6 mm cut length gives the highest wet tensile strength. A comparison of Samples 41, 42 and 43 to each other shows that increasing the percentage of partially drawn polyester core 2.0 dpf by 6 mm cut length bicomponent fiber in the middle layer from 60% to 80% increases both the wet tensile strength and wet elongation. Further increasing the level of partially drawn polyester core 2.0 dpf by 6 mm cut length bicomponent fiber in the middle layer from 80% to 100% does not increase wet elongation or wet tensile strength.

Example 6

Samples from Pilot Line with Binder for Higher Elongation and Lower Stiffness Structures In the present Example, raw materials were combined to form pilot samples.

The structure shown in Sample 46 was prepared on an M&J pilot scale airlaid manufacturing unit. FiberVisions (Varde, Denmark) AL-Adhesion-C bicomponent fiber, having a denier of 1.7 dpf and 4 mm fiber length was used. This bicomponent fiber had a core made of polypropylene and a sheath made of polyethylene.

Sample 46 was prepared in one pass through the airlaid pilot line utilizing one forming head. The forming head added a mixture of 11.81 gsm of FiberVisions AL-Adhesion-C bicomponent fiber (Varde, Denmark), having a denier of 1.7 dpf and 4 mm fiber length and 44.25 gsm of Weyerhaeuser NB416 fluff pulp (Federal Way, Wash.). The web was immediately compacted via a compaction roll. To the top side of this compacted web was then added via a high pressure spray system using a 50% aqueous solution 1.47 gsm dry weight of Celanese Emulsions Developmental Product 25-442A binder, which is a self-crosslinking vinyl acetate-ethylene (VAE) copolymer emulsion designed to impart a very soft feel with improved wet-elongation properties. Immediately after this the web was cured in a Through Air Tunnel Drier at a temperature of approximately 140-160° C. Immediately after this an additional 1.48 gsm dry weight of Celanese Emulsions Developmental Product 25-442A binder as a 50% aqueous solution was added to the opposite side of the web. Immediately after this the web was cured in a Through Air Tunnel Drier at a temperature of temperature of approximately 140-160° C. After this the web was wound and collected. The composition of Sample 46 is given in Table 38 below.

Samples 47, 48, 49, 50 and 51 were prepared similarly to Sample 46, but with the compositions given in Table 39, Table 40, Table 41, Table 42 and Table 43 respectively. The cross section of Samples 46-51 are shown in FIG. 7.

TABLE 38

Composition of the Pilot Sample 46

|  |  | 46 (gsm) |
|---|---|---|
| Binder | Celanese Emulsions Developmental Product 25-442A | 1.47 |

TABLE 38-continued

Composition of the Pilot Sample 46

| | | 46 (gsm) |
|---|---|---|
| Single Layer | Weyerhaeuser NB416 fluff pulp | 44.25 |
| | FiberVisions AL-Adhesion-C bicomponent fiber | 11.81 |
| Binder | Celanese Emulsions Developmental Product 25-442A | 1.47 |
| | Total BW | 59.00 |

TABLE 39

Composition of the Pilot Sample 47

| | | 47 (gsm) |
|---|---|---|
| Binder | Celanese Emulsions Developmental Product 25-442A | 2.95 |
| Single Layer | Weyerhaeuser NB416 fluff pulp | 41.30 |
| | FiberVisions AL-Adhesion-C bicomponent fiber | 11.80 |
| Binder | Celanese Emulsions Developmental Product 25-442A | 2.95 |
| | Total BW | 59.00 |

TABLE 40

Composition of the Pilot Sample 48

| | | 48 (gsm) |
|---|---|---|
| Binder | Celanese Emulsions Developmental Product 25-442A | 4.42 |
| Single Layer | Weyerhaeuser NB416 fluff pulp | 38.36 |
| | FiberVisions AL-Adhesion-C bicomponent fiber | 11.80 |
| Binder | Celanese Emulsions Developmental Product 25-442A | 4.42 |
| | Total BW | 59.00 |

TABLE 41

Composition of the Pilot Sample 49

| | | 49 (gsm) |
|---|---|---|
| Binder | Celanese Emulsions Elite 33 | 1.52 |
| Single Layer | Weyerhaeuser NB416 fluff pulp | 45.76 |
| | FiberVisions AL-Adhesion-C bicomponent fiber | 12.20 |
| Binder | Celanese Emulsions Elite 33 | 1.52 |
| | Total BW | 61.00 |

TABLE 42

Composition of the Pilot Sample 50

| | | 50 (gsm) |
|---|---|---|
| Binder | Celanese Emulsions Elite 33 | 3.00 |
| Single Layer | Weyerhaeuser NB416 fluff pulp | 42.00 |
| | FiberVisions AL-Adhesion-C bicomponent fiber | 12.00 |
| Binder | Celanese Emulsions Elite 33 | 3.00 |
| | Total BW | 60.00 |

TABLE 43

Composition of the Pilot Sample 51

| | | 51 (gsm) |
|---|---|---|
| Binder | Celanese Emulsions Elite 33 | 4.50 |
| Single Layer | Weyerhaeuser NB416 fluff pulp | 39.00 |
| | FiberVisions AL-Adhesion-C bicomponent fiber | 12.00 |
| Binder | Celanese Emulsions Elite 33 | 4.50 |
| | Total BW | 60.00 |

Table 44 summarizes the performance results of all the pilot samples incorporating Celanese Emulsions Developmental Product 25-442A binder.

TABLE 44

Summary of the Results of Pilot Samples 46-48

| Sample # | BW (gsm) | Binder % | CDW Tensile (g/in) | CDW Tensile (g/cm) | CDW Elongation (%) | CD Stiffness (mm) |
|---|---|---|---|---|---|---|
| 46 | 59.00 | 5% | 275 | 108 | 27 | 98 |
| 47 | 59.00 | 10% | 330 | 130 | 28 | 106 |
| 48 | 59.00 | 15% | 387 | 152 | 29 | 109 |

Table 45 summarizes the performance results of all the pilot samples incorporating Celanese Emulsions Elite 33 binder.

TABLE 45

Summary of the Results of Pilot Samples 49-51

| Sample # | BW (gsm) | Binder % | CDW Tensile (g/in) | CDW Tensile (g/cm) | CDW Elongation (%) | CD Stiffness (mm) |
|---|---|---|---|---|---|---|
| 49 | 61.00 | 5% | 262 | 103 | 23 | 137 |
| 50 | 60.00 | 10% | 391 | 154 | 21 | 137 |
| 51 | 60.00 | 15% | 535 | 211 | 23 | 138 |

All of the following comparisons take into account the various levels of binder, pulp and basis weight variations. A comparison of Samples 46, 47, and 48 using Celanese Emulsions Developmental Product 25-442A binder shows that they deliver up to 33% more cross directional wet elongation at the same add-on level while also reducing cross directional stiffness up to 33% in an airlaid substrate of the given design and composition relative to the Celanese Elite 33 binder. The Celanese Emulsion Developmental Product 25-442A binder gives reduced cross directional wet tensile strength relative to the Celanese Elite 33 binder when the add-on level is at 10% or higher, but has negligible impact when the binder add-on level is at 5%.

Example 7

Samples from Pilot Line for Partially Drawn Core Bicomponent Fibers Structures In the present Example, raw materials were combined to form pilot samples.

The structure shown in Sample 52 was prepared on a Dan-Web pilot scale airlaid manufacturing unit. Trevira T255 bicomponent fiber (Bobingen, Germany), having a denier of 2.0 dpf and 6 mm fiber length, and a partially drawn core was used. This bicomponent fiber had a core made of polyethylene terephthalate (PET) and a sheath made of polyethylene.

Sample 52 was prepared in one pass through the three forming head airlaid pilot line utilizing one forming head. The first forming head added a mixture of 59 gsm of Trevira T255 bicomponent fiber (Bobingen, Germany), having a denier of 2.0 dpf and 6 mm fiber length with a partially drawn core and 0 gsm of FOLEY FLUFFS® pulp (Buckeye Technologies Inc., Memphis, Tenn.). Immediately after this, the web was compacted via the compaction roll. Then the web was cured in a Moldow Through Air Tunnel Drier (Moldow Systems AS, Vaerloese, Denmark) at a temperature of temperature 145-155° C. After this the web was wound and collected. The machine speed was 10-20 meters/minute. The composition is given in Table 46 below. Samples 53, 54, 55, 56 and 57 were prepared similarly to Sample 52, but with the compositions given in Table 47, Table 48, Table 49, Table 50 and Table 51 respectively. The cross section of Sample 52 is shown in FIG. 9. The cross section of samples 53-57 are shown in FIG. 3.

TABLE 46

Composition of the Pilot Sample 52

| | | 52 (gsm) |
|---|---|---|
| Single Layer | FOLEY FLUFFS ® pulp | 0 |
| | Trevira T255 2.0 dpf partially drawn core bicomponent fiber | 59 |
| | Total BW | 59.0 |

TABLE 47

Composition of the Pilot Sample 53

| | | 53 (gsm) |
|---|---|---|
| Single Layer | FOLEY FLUFFS ® pulp | 6.1 |
| | Trevira T255 2.0 dpf partially drawn core bicomponent fiber | 60.4 |
| | Total BW | 66.5 |

TABLE 48

Composition of the Pilot Sample 54

| | | 54 (gsm) |
|---|---|---|
| Single Layer | FOLEY FLUFFS ® pulp | 8.1 |
| | Trevira T255 2.0 dpf partially drawn core bicomponent fiber | 43.4 |
| | Total BW | 51.5 |

TABLE 49

Composition of the Pilot Sample 55

| | | 55 (gsm) |
|---|---|---|
| Single Layer | FOLEY FLUFFS ® pulp | 13.3 |
| | Trevira T255 2.0 dpf partially drawn core bicomponent fiber | 45.7 |
| | Total BW | 59.0 |

TABLE 50

Composition of the Pilot Sample 56

| | | 56 (gsm) |
|---|---|---|
| Single Layer | FOLEY FLUFFS ® pulp | 14.8 |
| | Trevira T255 2.0 dpf partially drawn core bicomponent fiber | 45.2 |
| | Total BW | 61.0 |

TABLE 51

Composition of the Pilot Sample 57

| | | 57 (gsm) |
|---|---|---|
| Single Layer | FOLEY FLUFFS ® pulp | 20.3 |
| | Trevira T255 2.0 dpf partially drawn core bicomponent fiber | 39.7 |
| | Total BW | 60.0 |

Table 52 summarizes the performance results of all the pilot samples.

TABLE 52

Summary of the Results of Pilot Samples 52-57

| Sample # | BW (gsm) | Caliper (mm) | Bicomponent Fiber % | CDW Tensile (g/cm) | CDW Elongation (%) |
|---|---|---|---|---|---|
| 52 | 59.0 | 0.67 | 100.0 | 2561 | 58.9 |
| 53 | 66.5 | 1.04 | 90.9 | 2443 | 58.7 |
| 54 | 51.5 | 1.00 | 84.2 | 1734 | 57.9 |
| 55 | 59.0 | 1.14 | 77.4 | 1744 | 56.4 |
| 56 | 61.0 | 1.14 | 74.1 | 1536 | 54.2 |
| 57 | 60.0 | 1.15 | 66.1 | 1277 | 51.5 |

The results in Table 52 cover a wide range of basis weights and calipers which may make the CDW tensile strength results more difficult to interpret relative to each other. In order to facilitate interpretation of these results they can be normalized to a standard that is set as a basis weight of 60.0 gsm and a caliper of 1.00 mm. It is known in the art that increasing the basis weight of a web will cause the CDW tensile strength to increase. Thus, the normalization of the CDW tensile strength for basis weight, relative to the 60 gsm set point, is accomplished by multiplying the measured CDW tensile strength by 60 gsm and dividing by the measured basis weight. This compensates for a higher basis weight by reducing the CDW tensile strength if the basis weight is over 60 gsm and increasing the CDW tensile strength if the basis weight is under 60 gsm. It is also known within the art that decreasing the caliper of a web will increase the CDW tensile strength. Thus, the normalization of the CDW tensile strength for caliper, relative to the 1.00 mm set point, is accomplished by multiplying the measured CDW tensile strength by the caliper. This compensates for a higher caliper by increasing the CDW tensile strength if the caliper is over 1.00 mm and decreasing the CDW tensile strength if the caliper is below 1.00 mm. The normalized CDW tensile strength (CDW-N) can be expressed by the Normalization Equation for CDW Tensile Strength as given in the following equation:

$$M \times C \times 60 \text{ gsm}/BW = N$$

where "M" is the cross directional wet (CDW) tensile strength as measured in g/cm; where "C" is the caliper measured in mm;
where "BW" is the basis weight measured in gsm; and
where "N" the normalized cross directional wet (CDW) tensile strength in g/cm.

Thus, the results for CDW tensile strength in Table 52 can be normalized by using the Normalization Equation for CDW Tensile Strength to give the Normalized results found in Table 53.

Table 53 summarizes the Normalized performance results of all the pilot samples.

TABLE 53

Summary of the Normalized Results of Pilot Samples 52-57

| Sample # | BW (gsm) | Caliper (mm) | Bicomponent Fiber % | Normalized CDW Tensile (g/cm) | CDW Elongation (%) |
|---|---|---|---|---|---|
| 52 | 59.0 | 0.67 | 100.0 | 1745 | 58.9 |
| 53 | 66.5 | 1.04 | 90.9 | 2292 | 58.7 |
| 54 | 51.5 | 1.00 | 84.2 | 2020 | 57.9 |
| 55 | 59.0 | 1.14 | 77.4 | 2022 | 56.4 |
| 56 | 61.0 | 1.14 | 74.1 | 1722 | 54.2 |
| 57 | 60.0 | 1.15 | 66.1 | 1469 | 51.5 |

All of the following comparisons take into account the various levels of binder, pulp, basis weight and caliper variations for the CDW % Elongation results and the Normalized results for the CDW Tensile Strength. They are based on a comparison of Samples 52, 53, 54, 55, 56 and 57 as given in Table 52 and Table 53 and shown in FIG. 10 all of which contained Trevira T255 2.0 dpf partially drawn core bicomponent fiber at the levels given in Table 53. A comparison of Samples 52, 53, 54, 55, 56 and 57 shows that as the percentage of the bicomponent fiber is increased the CDW % Elongation also increases until it plateaus at a level of about 90% bicomponent fiber content. The CDW % Elongation increases minimally as the bicomponent fiber content is increased between 90% to 100%. A comparison of the Normalized CDW Tensile Strength as given in Table 53 shows that as the percentage of bicomponent fiber is increased the CDW Tensile Strength is also increased until the bicomponent fiber level is about 90% to 96%. As the bicomponent fiber level is further increased from about 96% to 100% the CDW Tensile Strength decreases significantly.

SUMMARY OF RESULTS

Table 54 provides an overall summary of the data obtained in Examples 1-7. In column one of Table 54, "#" refers to the Example numbers within the present application. In column two of Table 54, "Smp" refers to the sample numbers within the Examples. In column three, "Lyrs" refers to the number of layers within the sample. Within column three, 1+Ltx refers to one layer plus the addition of latex. Within column three, 5+Ltx refers to five layers plus the addition of latex.

In column four of Table 54, Composition—Total BW (gsm) refers to the total basis weight in grams per square meter of the composition. In column five, Composition-Fluff Pulp BW (gsm) refers to the basis weight in grams per square meter of the fluff pulp portion of the structure. In column six, Composition Fluff Pulp Wt (%) refers to the weight percent of the fluff pulp in the overall composition of the structure.

In column seven of Table 54, Composition Bicomponent Fiber BW (gsm) refers to the basis weight in grams per square meter of the bicomponent fiber portion of the structure. In column eight, Composition Bicomponent Fiber Wt % refers to the weight percent of the bicomponent fiber in the overall composition of the structure. In column nine of Table 54, Composition Bicomponent Fiber Type refers to the type of bicomponent fiber used by the manufacturer and type. Within column nine of Table 54, T-1661 refers to Trevira type 1661 bicomponent fiber.

TABLE 54

Summary of Results

| | | | Composition | | | | | | | | | | Cross Directional Properties | | | |
|---|---|---|---|---|---|---|---|---|---|---|---|---|---|---|---|---|
| | | | Total | Fluff Pulp | | Bicomponent Fiber | | | | Binder | | | Wet | Wet | | Wet Ten |
| Example | | | BW | BW | Wt % | BW | Wt % | | Len | BW | Wt % | | Tensile | Elong | Stiff | Normal |
| # | Smp | Lyrs | (gsm) | (gsm) | (%) | (gsm) | (%) | Type | (mm) | (gsm) | (%) | Type | (g/cm) | (%) | (mm) | (g/cm) |
| 1 | 1 | 1 | 54.64 | 40.46 | 74.0 | 14.18 | 26.0 | T-1661 | 6 | 0 | 0 | n/a | 166 | n/a | n/a | n/a |
| 1 | 2 | 1 | 53.79 | 40.03 | 74.4 | 13.76 | 25.6 | T-1661 | 6 | 0 | 0 | n/a | 173 | n/a | n/a | n/a |
| 1 | 3 | 1 | 53.90 | 40.63 | 75.4 | 13.27 | 24.6 | T-1661 | 6 | 0 | 0 | n/a | 154 | n/a | n/a | n/a |
| 1 | 4 | 1 | 52.89 | 39.02 | 73.8 | 13.87 | 26.2 | T-1661 | 6 | 0 | 0 | n/a | 148 | n/a | n/a | n/a |
| 1 | 5 | 1 | 54.25 | 38.80 | 71.5 | 15.45 | 28.5 | T-1661 | 6 | 0 | 0 | n/a | 186 | n/a | n/a | n/a |
| 1 | 6 | 1 | 52.35 | 37.35 | 71.3 | 15.00 | 28.7 | T-1661 | 6 | 0 | 0 | n/a | 211 | n/a | n/a | n/a |
| 1 | 7 | 1 | 51.31 | 36.54 | 71.2 | 14.77 | 28.8 | T-1661 | 6 | 0 | 0 | n/a | 239 | n/a | n/a | n/a |

TABLE 54-continued

Summary of Results

| | | | Composition | | | | | | | | | Cross Directional Properties | | | Wet |
|---|---|---|---|---|---|---|---|---|---|---|---|---|---|---|---|
| | | | Total | Fluff Pulp | | Bicomponent Fiber | | | Binder | | | Wet | Wet | | Wet Ten |
| Example | | | BW | BW | Wt % | BW | Wt % | | Len | BW | Wt % | | Tensile | Elong | Stiff | Normal |
| # | Smp | Lyrs | (gsm) | (gsm) | (%) | (gsm) | (%) | Type | (mm) | (gsm) | (%) | Type | (g/cm) | (%) | (mm) | (g/cm) |
|---|---|---|---|---|---|---|---|---|---|---|---|---|---|---|---|---|
| 1 | 8 | 1 | 50.84 | 36.14 | 71.1 | 14.70 | 28.9 | T-1661 | 6 | 0 | 0 | n/a | 240 | n/a | n/a | n/a |
| 1 | 9 | 1 | 60.53 | 46.06 | 76.1 | 14.47 | 23.9 | T-1661 | 6 | 0 | 0 | n/a | 194 | n/a | n/a | n/a |
| 1 | 10 | 1 | 59.06 | 44.88 | 76.0 | 14.18 | 24.0 | T-1661 | 6 | 0 | 0 | n/a | 162 | n/a | n/a | n/a |
| 2 | 11 | 2 | 57.58 | 40.22 | 69.9 | 17.36 | 30.15 | T-1661 | 6 | 0 | 0 | n/a | 420 | n/a | n/a | n/a |
| 2 | 12 | 2 | 63.43 | 47.50 | 74.9 | 15.93 | 25.11 | T-1661 | 6 | 0 | 0 | n/a | 296 | n/a | n/a | n/a |
| 2 | 13 | 2 | 66.65 | 49.56 | 74.4 | 17.09 | 25.64 | T-1661 | 6 | 0 | 0 | n/a | 345 | n/a | n/a | n/a |
| 2 | 14 | 2 | 58.24 | 40.30 | 69.2 | 17.94 | 30.81 | T-1661 | 6 | 0 | 0 | n/a | 455 | n/a | n/a | n/a |
| 2 | 15 | 2 | 53.55 | 40.96 | 76.5 | 12.59 | 23.52 | T-1661 | 6 | 0 | 0 | n/a | 252 | n/a | n/a | n/a |
| 2 | 16 | 2 | 67.81 | 53.82 | 79.4 | 13.99 | 20.63 | T-1661 | 6 | 0 | 0 | n/a | 264 | n/a | n/a | n/a |
| 2 | 17 | 2 | 56.69 | 43.13 | 76.1 | 13.56 | 23.92 | T-1661 | 6 | 0 | 0 | n/a | 285 | n/a | n/a | n/a |
| 2 | 18 | 2 | 54.48 | 39.21 | 72.0 | 15.27 | 28.02 | T-1661 | 6 | 0 | 0 | n/a | 399 | n/a | n/a | n/a |
| 2 | 19 | 2 | 57.78 | 42.86 | 74.2 | 14.92 | 25.82 | T-1661 | 6 | 0 | 0 | n/a | 366 | n/a | n/a | n/a |
| 2 | 20 | 2 | 64.98 | 47.47 | 73.1 | 17.51 | 26.95 | T-1661 | 6 | 0 | 0 | n/a | 402 | n/a | n/a | n/a |
| 3 | 21 | 1 | 54.35 | 39.99 | 73.6 | 14.36 | 26.5 | T-1661 | 6 | 0 | 0 | n/a | 181 | n/a | n/a | n/a |
| 3 | 22 | 1 | 60.12 | 47.37 | 78.8 | 12.75 | 21.3 | T-4178 | 12 | 0 | 0 | n/a | 209 | n/a | n/a | n/a |
| 3 | 23 | 1 | 63.50 | 47.15 | 74.3 | 16.34 | 25.7 | T-4178 | 12 | 0 | 0 | n/a | 256 | n/a | n/a | n/a |
| 3 | 24 | 1 | 59.90 | 41.45 | 69.2 | 18.45 | 30.7 | T-4178 | 12 | 0 | 0 | n/a | 327 | n/a | n/a | n/a |
| 4 | 25 | 5 + Ltx | 60.60 | 39.6 | 65.3 | 18.4 | 30.4 | T-1661 | 6 | 2.6 | 4.3 | AF-192 | n/a | n/a | n/a | n/a |
| 4 | 26 | 5 + Ltx | 58.00 | 37.0 | 63.8 | 18.6 | 32.1 | T-1661 T-4234 | 6 8 | 2.4 | 4.1 | AF-192 | n/a | n/a | n/a | n/a |
| 4 | 27 | 5 + Ltx | 58.40 | 37.7 | 64.6 | 17.5 | 30.0 | T-1661 T-4178 | 6 12 | 3.2 | 5.5 | AF-192 | n/a | n/a | n/a | n/a |
| 4B | 25B | 5 + Ltx | 60.60 | 39.6 | 65.3 | 18.4 | 30.4 | T-1661 I-T255 | 6 6 | 2.6 | 4.3 | AF-124 | 230 | n/a | n/a | n/a |
| 4B | 26B | 5 + Ltx | 58.00 | 37.0 | 63.8 | 18.6 | 32.1 | T-1661 T-4234 I-T255 | 6 8 6 | 2.4 | 4.1 | AF-124 | 266 | | | |
| 4B | 27B | 5 + Ltx | 58.40 | 37.7 | 64.6 | 17.5 | 30.0 | T-1661 T-4178 I-T255 | 6 12 6 | 3.2 | 5.5 | AF-124 | 290 | n/a | n/a | n/a |
| 5 | 28 | 3 | 69.73 | 41.68 | 59.8 | 28.05 | 40.2 | T-1661 T-265P | 6 6 | 0 | 0 | n/a | 569 | 44.6 | n/a | n/a |
| 5 | 29 | 3 | 70.22 | 39.04 | 55.6 | 31.18 | 44.4 | T-1661 T-265P | 6 6 | 0 | 0 | n/a | 681 | 43.8 | n/a | n/a |
| 5 | 30 | 1 | 73.82 | 55.17 | 74.7 | 18.65 | 25.3 | T-265P | 6 | 0 | 0 | n/a | 307 | 41.4 | n/a | n/a |
| 5 | 31 | 3 | 63.07 | 39.62 | 62.8 | 23.45 | 37.2 | T-1661 | 6 | 0 | 0 | n/a | 372 | 40.6 | n/a | n/a |
| 5 | 32 | 3 | 62.45 | 38.52 | 61.7 | 23.92 | 38.3 | T-1661 T-255P | 6 6 | 0 | 0 | n/a | 378 | 37.6 | n/a | n/a |
| 5 | 33 | 1 | 70.05 | 54.13 | 77.3 | 15.92 | 22.7 | T-255P | 6 | 0 | 0 | n/a | 167 | 33.6 | n/a | n/a |
| 5 | 34 | 3 | 64.93 | 38.60 | 59.4 | 26.33 | 40.6 | T-1661 T-255P | 6 6 | 0 | 0 | n/a | 405 | 39.0 | n/a | n/a |
| 5 | 35 | 3 | 71.69 | 40.69 | 56.8 | 31.00 | 43.2 | T-1661 T-255P | 6 6 | 0 | 0 | n/a | 591 | 40.4 | n/a | n/a |
| 5 | 36 | 1 | 66.97 | 49.64 | 74.1 | 17.33 | 25.9 | T-255P | 6 | 0 | 0 | n/a | 211 | 35.3 | n/a | n/a |
| 5 | 37 | 3 | 63.76 | 31.16 | 48.9 | 32.60 | 51.1 | T-1661 | 6 | 0 | 0 | n/a | 447 | 33.5 | n/a | n/a |
| 5 | 38 | 3 | 63.47 | 39.26 | 61.9 | 24.21 | 38.1 | T-1661 | 6 | 0 | 0 | n/a | 352 | 32.3 | n/a | n/a |
| 5 | 39 | 1 | 54.85 | 43.21 | 78.8 | 11.64 | 21.2 | T-1661 | 6 | 0 | 0 | n/a | 125 | 28.6 | n/a | n/a |
| 5 | 40 | 3 | 54.61 | 36.64 | 67.1 | 17.97 | 32.9 | T-1661 T-255P | 6 6 | 0 | 0 | n/a | 404 | 50.5 | n/a | n/a |
| 5 | 41 | 3 | 65.63 | 41.40 | 63.1 | 24.23 | 36.9 | T-1661 T-255P | 6 6 | 0 | 0 | n/a | 617 | 54.1 | n/a | n/a |
| 5 | 42 | 3 | 56.87 | 37.40 | 65.8 | 19.47 | 34.2 | T-1661 T-255P | 6 6 | 0 | 0 | n/a | 353 | 43.4 | n/a | n/a |
| 5 | 43 | 3 | 59.29 | 39.92 | 67.3 | 19.37 | 32.7 | T-1661 | 6 6 | 0 | 0 | n/a | 416 | 35.7 | n/a | n/a |
| 5 | 44 | 3 | 71.20 | 48.97 | 68.8 | 22.24 | 31.2 | T-1661 | 6 6 | 0 | 0 | n/a | 365 | 36.0 | n/a | n/a |
| 5 | 45 | 3 | 53.05 | 37.61 | 70.9 | 15.44 | 29.1 | T-1661 | 6 6 | 0 | 0 | n/a | 220 | 33.9 | n/a | n/a |
| 6 | 46 | 1 + Ltx | 59.0 | 44.35 | 75.2 | 11.81 | 20.0 | F-ALC | 4 | 2.94 | 5.0 | 25-442A | 108 | 27.0 | 98 | n/a |
| 6 | 47 | 1 + Ltx | 59.0 | 41.30 | 70.0 | 11.80 | 20.0 | F-ALC | 4 | 5.90 | 10.0 | 25-442A | 130 | 28.0 | 106 | n/a |
| 6 | 48 | 1 + Ltx | 59.0 | 38.36 | 65.0 | 11.80 | 20.0 | F-ALC | 4 | 8.84 | 15.0 | 25-442A | 152 | 29.0 | 109 | n/a |
| 6 | 49 | 1 + Ltx | 61.0 | 45.76 | 75.0 | 12.20 | 20.0 | F-ALC | 4 | 3.04 | 5.0 | Elite 33 | 103 | 23.0 | 137 | n/a |
| 6 | 50 | 1 + Ltx | 60.0 | 42.00 | 70.0 | 12.00 | 20.0 | F-ALC | 4 | 6.00 | 10.0 | Elite 33 | 154 | 21.0 | 137 | n/a |
| 6 | 51 | 1 + Ltx | 60.0 | 39.00 | 65.0 | 12.00 | 20.0 | F-ALC | 4 | 9.00 | 15.0 | Elite 33 | 211 | 23.0 | 138 | n/a |
| 7 | 52 | 1 | 59.00 | 0.00 | 0.0 | 59.00 | 100.0 | T-255P | 6 | 0 | 0 | n/a | 2561 | 58.9 | n/a | 1745 |
| 7 | 53 | 1 | 66.50 | 6.10 | 9.2 | 60.40 | 90.8 | T-255P | 6 | 0 | 0 | n/a | 2443 | 58.7 | n/a | 2292 |

TABLE 54-continued

Summary of Results

| | | | Composition | | | | | | | | | Cross Directional Properties | | | |
|---|---|---|---|---|---|---|---|---|---|---|---|---|---|---|---|
| | | Total | Fluff Pulp | | Bicomponent Fiber | | | | Binder | | | Wet | Wet | | Wet Ten |
| Example | | BW | BW | Wt % | BW | Wt % | | Len | BW | Wt % | | Tensile | Elong | Stiff | Normal |
| # | Smp | Lyrs | (gsm) | (gsm) | (%) | (gsm) | (%) | Type | (mm) | (gsm) | (%) | Type | (g/cm) | (%) | (mm) | (g/cm) |
| 7 | 54 | 1 | 51.50 | 8.10 | 15.7 | 43.40 | 84.3 | T-255P | 6 | 0 | 0 | n/a | 1734 | 57.9 | n/a | 2020 |
| 7 | 55 | 1 | 59.00 | 13.30 | 22.5 | 45.70 | 77.5 | T-255P | 6 | 0 | 0 | n/a | 1744 | 56.4 | n/a | 2022 |
| 7 | 56 | 1 | 61.00 | 14.80 | 24.3 | 45.20 | 74.1 | T-255P | 6 | 0 | 0 | n/a | 1536 | 54.2 | n/a | 1722 |
| 7 | 57 | 1 | 60.00 | 20.30 | 33.8 | 39.70 | 66.2 | T-255P | 6 | 0 | 0 | n/a | 1277 | 51.5 | n/a | 1469 |

Within column nine of Table 54, 1-255 refers to Invista type 255 bicomponent fiber. Within column nine of Table 54, T-4178 refers to Trevira type 4178 bicomponent fiber. Within column nine, T-255P refers to Trevira type 255P bicomponent fiber. Within column nine of Table 54, F-ALC refers to ES FiberVisions AL-Adhesion-C bicomponent fiber. Within column nine, T-4234 refers to Trevira type 4234 bicomponent fiber.

In column ten of Table 54, Composition Bicomponent Fiber Len (mm) refers to the length of the bicomponent fiber in millimeters. In column eleven, Composition Binder BW (gsm) refers to the basis weight in grams per square meter of the binder portion of the structure. In column twelve, Composition Binder Wt % refers to the weight percent of the binder in the overall composition of the structure.

In column thirteen, Composition Binder Type refers to the type of binder used by the manufacturer and type. Within column thirteen of Table 54, A-192 refers to Air Products Airflex 192 binder; A-124 refers to Air Products Airflex 124 binder; 25-442A refers to Celanese Emulsions Development Product 25-442A binder; Elite 33 refers to Celanese Emulsions Elite 33 binder; and n/a refers to not applicable in that no binder was used on the product.

In column fourteen of Table 54, Cross Directional Properties Wet Tensile (g/cm) refers to the cross directional wet tensile strength in grams per centimeter. In column fifteen, Cross Directional Properties Wet Elong (%) refers to the amount of elongation in the cross direction in the wet state. In column sixteen, Cross Directional Properties Stiff (mm) refers to the angular bend stiffness in the cross direction in millimeters in the dry state. In column seventeen, Cross Directional Properties Wet Ten Normal (g/cm) refers to the normalized cross directional wet tensile strength in grams per centimeter that is calculated using the formula noted above.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A high strength multistrata nonwoven wipe material comprising:
    (A) from about 45 to about 95 weight percent matrix fibers selected from the group consisting of cellulosic fibers, synthetic fibers, and a mixture of cellulosic fibers and synthetic fibers;
    (B) from about 5 to about 55 weight percent bicomponent fiber, wherein the bicomponent fiber has a length of from about 3 mm to about 36 mm; and
    (C) optionally, from 0 to about 15 weight percent binder, wherein the weight percentages are based on the total weight of the material, and wherein the material has
    (D) a basis weight of from about 40 gsm to about 100 gsm,
    (E) a density of from about 0.03 to about 0.15 g/cc, and
    (F) a CDW tensile strength of about 252 g/cm or greater, and wherein the material comprises two or more strata, and has at least one stratum comprising from about 60 weight percent to about 100 weight percent bicomponent fibers, and wherein the composition of any one stratum is different from at least one adjacent stratum, and wherein the material has two outer strata and one or more inner strata and the weight percent bicomponent fiber of one inner stratum is from about 70 weight percent to about 100 weight percent bicomponent fiber based on the total weight of the one inner stratum.

2. The material of claim 1, wherein the material has two outer strata and one or more inner strata and the weight percent bicomponent fiber of one inner stratum is from about 70 weight percent to about 95 weight percent bicomponent fiber based on the total weight of the one inner stratum.

3. The material of claim 1, wherein the material has two outer strata and one or more inner strata and the weight percent bicomponent fiber of one inner stratum is from about 75 weight percent to about 95 weight percent bicomponent fiber based on the total weight of the one inner stratum.

4. The material of claim 1, wherein the material has two outer strata and one or more inner strata and the weight percent bicomponent fiber of one inner stratum is from about 80 weight percent to about 90 weight percent bicomponent fiber based on the total weight of the one inner stratum.

5. The material of claim 1, wherein the material has two outer strata and one or more inner strata and the weight percent bicomponent fiber of one inner stratum is from about 90 weight percent to about 100 weight percent bicomponent fiber based on the total weight of the one inner stratum.

6. A high strength multistrata nonwoven wipe material comprising:
    (A) from about 45 to about 95 weight percent matrix fibers selected from the group consisting of cellulosic fibers, synthetic fibers, and a mixture of cellulosic fibers and synthetic fibers;

(B) from about 5 to about 55 weight percent bicomponent fiber, wherein the bicomponent fiber has a length of from about 3 mm to about 36 mm; and
(C) optionally, from 0 to about 15 weight percent binder, wherein the weight percentages are based on the total weight of the material, and wherein the material has
(D) a basis weight of from about 40 gsm to about 100 gsm,
(E) a density of from about 0.03 to about 0.15 g/cc, and
(F) a CDW tensile strength of about 252 g/cm or greater, and wherein the material comprises two or more strata, and has at least one stratum comprising from about 60 weight percent to about 100 weight percent bicomponent fibers, and wherein the composition of any one stratum is different from at least one adjacent stratum, and wherein the material has two outer strata and one or more inner strata and the weight percent bicomponent fiber of one outer stratum is from about 70 weight percent to about 100 weight percent bicomponent fiber based on the total weight of the outer stratum.

7. The material of claim 1, wherein the bicomponent fibers have a length of about 6 mm or greater.

8. The material claim 7, wherein the bicomponent fibers have a length of about 8 mm or greater.

9. The material claim 8, wherein the bicomponent fibers have a length of about 10 mm or greater.

10. The material of claim 9, wherein the bicomponent fibers have a length of about 12 mm or greater.

11. The material of claim 1, wherein the CDW tensile strength of the nonwoven material is equal to about 394 g/cm or greater.

12. The material of claim 11, wherein the CDW tensile strength of the nonwoven material is equal to about 591 g/cm or greater.

13. The material of claim 12, wherein the CDW tensile strength of the nonwoven material is equal to about 787 g/cm or greater.

14. The material of claim 1, wherein the material has been produced by an airlaid process.

15. The material of claim 1, wherein the bicomponent fiber has a partially drawn core.

* * * * *